US007945331B2

(12) United States Patent
Vilims

(10) Patent No.: US 7,945,331 B2
(45) Date of Patent: May 17, 2011

(54) COMBINATION ELECTRICAL STIMULATING AND INFUSION MEDICAL DEVICE AND METHOD

(75) Inventor: Bradley D. Vilims, Evergreen, CO (US)

(73) Assignee: Bradley D. Vilims, Evergreen, CO (US)

( * ) Notice: Subject to any disclaimer, the term of this patent is extended or adjusted under 35 U.S.C. 154(b) by 732 days.

(21) Appl. No.: 11/678,516

(22) Filed: Feb. 23, 2007

(65) Prior Publication Data

US 2007/0135881 A1 Jun. 14, 2007

Related U.S. Application Data

(63) Continuation-in-part of application No. 11/107,553, filed on Apr. 14, 2005, now abandoned, which is a continuation-in-part of application No. 11/033,591, filed on Jan. 11, 2005, now Pat. No. 7,386,350.

(51) Int. Cl.
*A61N 1/34* (2006.01)
*A61N 1/08* (2006.01)
(52) U.S. Cl. .......................................... 607/46; 607/117
(58) Field of Classification Search .................... 607/46, 607/117, 118; 606/41
See application file for complete search history.

(56) References Cited

U.S. PATENT DOCUMENTS

| 4,612,934 | A | 9/1986 | Borkan |
|---|---|---|---|
| 5,255,691 | A | 10/1993 | Otten |
| 5,342,357 | A | 8/1994 | Nardella |
| 5,397,338 | A | 3/1995 | Grey et al. |
| 5,423,877 | A | 6/1995 | Mackey |
| 5,951,546 | A | 9/1999 | Lorentzen |
| 6,002,964 | A | 12/1999 | Feler et al. |
| 6,053,916 | A | 4/2000 | Moore |
| 6,104,957 | A | 8/2000 | Alo et al. |
| 6,136,021 | A | 10/2000 | Tockman et al. |
| 6,146,380 | A | 11/2000 | Racz et al. |
| 6,148,222 | A | 11/2000 | Ramsey |
| 6,161,047 | A | 12/2000 | King et al. |

(Continued)

FOREIGN PATENT DOCUMENTS

WO    WO 81/03272    11/1981

(Continued)

OTHER PUBLICATIONS

Freeman, et al., "Does intradiscal electrothermal therapy denervate and repair experimentally induced posterolateral annular tears in an animal model?", Spine, Dec. 1, 2003, vol. 28, No. 23, pp. 2602-2608.

(Continued)

*Primary Examiner* — Carl H. Layno
*Assistant Examiner* — Tammie K Heller
(74) *Attorney, Agent, or Firm* — Sheridan Ross, P.C.

(57) ABSTRACT

A combined electrical and chemical stimulation lead is especially adapted for providing treatment to the spine and nervous system. The stimulation lead includes electrodes that may be selectively positioned along various portions of the stimulation lead in order to precisely direct electrical energy to ablate or electrically stimulate the target tissue. Embodiments of the stimulation lead include single or multiple lead elements. The multiple lead element embodiments can be selectively deployed to cover a targeted area. The lead may also includes central infusion passageway(s) or lumen(s) that communicates with various infusion ports spaced at selected locations along the lead to thereby direct the infusion of nutrients/chemicals to the target tissue. One embodiment utilizes a dissolvable matrix for infusion as opposed to remote delivery through an infusion pump.

3 Claims, 19 Drawing Sheets

U.S. PATENT DOCUMENTS

| | | | |
|---|---|---|---|
| 6,263,225 B1 | 7/2001 | Howard, III | |
| 6,277,112 B1 | 8/2001 | Underwood et al. | |
| 6,379,349 B1 | 4/2002 | Muller et al. | |
| 6,562,033 B2 | 5/2003 | Shah et al. | |
| 6,656,174 B1 | 12/2003 | Hegde et al. | |
| 6,662,055 B1 | 12/2003 | Prutchi | |
| 6,735,474 B1 | 5/2004 | Loeb et al. | |
| 6,827,716 B2 | 12/2004 | Ryan et al. | |
| 6,832,115 B2 | 12/2004 | Borkan | |
| 6,845,267 B2 | 1/2005 | Harrison | |
| 6,847,849 B2 | 1/2005 | Mamo et al. | |
| 6,902,547 B2 | 6/2005 | Aves et al. | |
| 6,921,403 B2 | 7/2005 | Cragg et al. | |
| 6,936,024 B1 | 8/2005 | Houser | |
| 7,014,633 B2 | 3/2006 | Cragg | |
| 7,065,412 B2 | 6/2006 | Swoyer et al. | |
| 7,069,087 B2 | 6/2006 | Sharkey et al. | |
| 7,069,094 B2 | 6/2006 | Kubota et al. | |
| 7,169,146 B2 | 1/2007 | Truckai et al. | |
| 7,276,063 B2 | 10/2007 | Davison et al. | |
| 7,369,894 B2 | 5/2008 | Gerber | |
| 7,422,586 B2 | 9/2008 | Morris et al. | |
| 7,449,019 B2 | 11/2008 | Uchida et al. | |
| 7,462,178 B2 | 12/2008 | Woloszko et al. | |
| 7,771,422 B2 | 8/2010 | Auge et al. | |
| 7,819,869 B2 | 10/2010 | Godara et al. | |
| 2003/0181964 A1 | 9/2003 | Sharkey et al. | |
| 2003/0195509 A1 | 10/2003 | Edwards et al. | |
| 2003/0195518 A1 | 10/2003 | Cragg | |
| 2003/0195604 A1 | 10/2003 | Ingle et al. | |
| 2003/0225331 A1 | 12/2003 | Diederich et al. | |
| 2004/0015202 A1 | 1/2004 | Chandler, III et al. | |
| 2004/0039425 A1 | 2/2004 | Greenwood-VanMeerveld | |
| 2004/0127965 A1 | 7/2004 | Borkan | |
| 2004/0230273 A1 | 11/2004 | Cates et al. | |
| 2004/0236388 A1 | 11/2004 | Gielen et al. | |
| 2004/0243206 A1 | 12/2004 | Tadlock | |
| 2004/0260277 A1 | 12/2004 | Maguire | |
| 2005/0096718 A1 | 5/2005 | Gerber et al. | |
| 2005/0177209 A1 | 8/2005 | Leung et al. | |
| 2005/0177211 A1 | 8/2005 | Leung et al. | |
| 2005/0240238 A1 | 10/2005 | Mamo et al. | |
| 2005/0277918 A1 | 12/2005 | Shah et al. | |
| 2006/0020297 A1 | 1/2006 | Gerber et al. | |
| 2006/0106376 A1 | 5/2006 | Godara et al. | |
| 2006/0155342 A1 | 7/2006 | Vilims | |
| 2006/0155343 A1 | 7/2006 | Vilims | |
| 2006/0217705 A1 | 9/2006 | Godara et al. | |
| 2006/0259026 A1 | 11/2006 | Godara et al. | |
| 2007/0055316 A1 | 3/2007 | Godara et al. | |
| 2007/0156136 A1 | 7/2007 | Godara et al. | |
| 2007/0179536 A1 | 8/2007 | Vilims | |
| 2008/0009927 A1 | 1/2008 | Vilims | |
| 2008/0172117 A1 | 7/2008 | Skubitz et al. | |
| 2008/0200972 A1 | 8/2008 | Vilims et al. | |

FOREIGN PATENT DOCUMENTS

| | | |
|---|---|---|
| WO | WO 94/02077 | 2/1994 |
| WO | WO 95/10320 | 4/1995 |
| WO | WO 98/19613 | 5/1998 |
| WO | WO 99/43263 | 9/1999 |

OTHER PUBLICATIONS

Extended European Search Report for European Patent Application No. 08151981.1, dated Dec. 9, 2008.
U.S. Appl. No. 12/340,092, filed Dec. 19, 2008, Vilims.
Partial European Search Report for European Patent Application No. 08101856.6, mailed Jul. 3, 2008.
Partial European Search Report for European Patent Application No. 08151981, mailed Jul. 16, 2008.
International Preliminary Report on Patentability for International (PCT) Patent Application No. PCT/US06/00312, issued Jul. 17, 2007.
Supplementary European Search Report for European Patent Application No. 06717501, mailed Aug. 20, 2008.
Partial European Search Report for European Patent Application No. 08101856.6, mailed Oct. 28, 2008.
Ahadian, "Pulsed radiofrequency neurotomy: advances in pain medicine," Current Pain and Headache Reports, 2004, vol. 8, pp. 34-40.
Akatov et al., "Percutaneous radiofrequency destruction of the obturator nerve for treatment of pain caused by coxarthrosis," Stereotact Funct Neurosurg, 1997, vol. 69(1-4 Pt 2), pp. 278-280 (Abstract only).
Anis et al., "Use of radio-frequency ablation for the palliative treatment of sacral chordoma," Am. J. Neuronadiol, 2004, vol. 25, pp. 1589-1591.
Atlihan et al., "Anatomy of the Anterior Sacroiliac Joint With Reference to Lumbosacral Nerves," Clinical Orthopaedics and Related Research, 2000, No. 376, pp. 236-241.
Buijs et al., "Radiofrequency treatment of sacroiliac joint-related pain aimed at the first three sacral dorsal rami: a minimal approach," The Pain Clinic, 2004, vol. 16(2), pp. 139-146.
Calvillo et al., "Anatomy and Pathophysiology of the Sacroiliac Joint," Current Review of Pain, 2000, vol. 4, pp. 356-361.
Cohen et al., "Lateral Branch Blocks as a Treatment for Sacroiliac Joint Pain: A Pilot Study," Regional Anesthesia and Pain Medicine, 2003, vol. 28(2), pp. 113-119.
Cohen et al., "Pulsed radiofrequency as a treatment for groin pain and orchialgia," Urology, 2003, vol. 61(3), pp. 645xxi-xxiii.
Cohen, "Sacroiliac Joint Pain: A Comprehensive Review of Anatomy, Diagnosis, and Treatment," Anesthesia & Analgesia, 2005, vol. 101(5), pp. 1440-1453.
Cole et al., "The Sacroiliac Joint: A Functional Approach," Critical Reviews in Physical and Rehabilitation Medicine, 1996, vol. 8(1&2), pp. 125-152.
Conaghan et al., "Sacral nerve stimulation can be successful in patients with ultrasound evidence of external anal sphincter disruption," Diseases of the Colon and Rectum, 2005, vol. 48(8), pp. 1610-1614.
Davis et al., "Radiofrequency Treatment in the United States," Pain Practice, 2002, vol. 2(3), pp. 192-194.
Deer, "Chapter 6: Injections for the Diagnosis and Treatment of Spinal Pain," American Society of Anesthesiologists, Inc., 2004, vol. 32, pp. 53-69.
Dreyfuss et al., "Chapter 32: Radiofrequency Neurotomy of the Zygapophyseal and Sacroiliac Joints," Pain Procedures, 2000, pp. 395-420.
Ebraheim et al., "Anatomic Considerations for Posterior Approach to the Sacroiliac Joint," Spine, 1996, vol. 21(23), pp. 2709-2712.
Ferrante et al., "Radiofrequency sacroiliac joint denervation for sacroiliac syndrome," Regional Anesthesia and Pain Medicine, 2001, vol. 26(2), pp. 137-142.
Fortin et al., "Three Pathways between the Sacroiliac Joint and Neural Structures," Am. J. Neruoradiol., 1999, vol. 20, pp. 1429-1434.
Fortin et al., "Sacroiliac Joint Innervation and Pain," The American Journal of Orthopedics, 1999, pp. 687-690.
Fukui et al., "Successful relief of hip joint pain by percutaneous radiofrequency nerve thermocoagulation in a patient with contraindications for hip arthroplasty," Journal of Anesthesia, 2001, vol. 15, pp. 173-175.
Gevargez et al., "CT-guided percutaneous radiofrequency denervation of the sacroiliac joint," Eur Radiol., 2002, vol. 12, pp. 1360-1365.
Gopalani et al., "A novel technique for treating nonsurgical hip pain with radiofrequency lesioning of the sensory branches of the obturator and femoral nerves: a case report," Archives of Physical Medicine and Rehabilitation, Poster 102, 2003, vol. 84, A23.
Jiang et al., "Comparison between radiofrequency coagulation plus small needle knife and single method in treatment of sacrolumbar pain," Chinese Journal of Clinical Rehabilitation, 2003, vol. 7(20), pp. 2844-2845 (Abstract only).
Kawaguchi et al., "Percutaneous radiofrequency lesioning of sensory branches of the obturator and femoral nerves for the treatment of hip joint pain," Regional Anesthesia and Pain Medicine, 2001, vol. 26(6), pp. 576-581.
Kirkham et al., "Neuromodulation through sacral nerve roots 2 to 4 with a Finetech-Brindley sacral posterior and anterior root stimulator," Spinal Cord, 2002, vol. 40(6), pp. 272-281.

Kirsch et al., "Proton radiotherapy for Hodgkin's disease in the sacrum," Lancet Oncology, 2005, vol. 6, pp. 532-533.

Kline et al., "Chapter 19: Radiofrequency techniques in clinical practice," Interventional Pain Management, 2001, pp. 243-290 (2001).

Leng et al., "How sacral nerve stimulation neuromodulation works," Urol. Clin. North. Am., 2005, vol. 32(1), pp. 11-18 (Abstract only).

Liguoro et al., "The Posterior Sacral Foramina: An Anatomical Study," 1999, J. Anat., vol. 195, pp. 301-304.

Murata et al., "Origin and pathway of sensory nerve fibers to the ventral and dorsal sides of the sacroiliac joint in rats," Journal of Orthopaedic Research, 2001, vol. 19, pp. 379-383.

Plancarte et al., "Radiofrequency Procedures for Sacral and Pelvic Region Pain," Pain Practice, 2002, vol. 2(3), pp. 248-249.

Pino et al., "Morphologic analysis of bipolar radiofrequency lesions: implications for treatment of the sacroiliac joint," Regional Anesthesia and Pain Medicine, 2005, vol. 30(4), pp. 335-338.

Raj et al., "Executive Summary: The Current Status of the Practice of Radiofrequency in the World," Pain Practice, 2002, vol. 2(3), pp. 176-179.

Simon, "Chapter 50: Sacroiliac joint injection and low back pain," Interventional Pain Management, 2001, pp. 535-539.

Slipman et al., "Sacroiliac Joint Syndrome," Pain Physician, 2001, vol. 4(2), pp. 143-152.

Valleylab-RF Pain Management System, Sep. 16, 2004, available at internet archives, http://www.valleylab.com/static/pain/products-generator.html, 2 pages.

Van Zundert et al. "Application of Radiofrequency Treatment in Practical Pain Management: State of the art," Pain Practice, 2002, vol. 2(3), pp. 269-278.

Yin et al., "Sensory stimulation-guided sacroiliac joint radiofrequency neurotomy: technique based on neuroanatomy of the dorsal sacral plexus," Spine, 2003, vol. 28(20), pp. 2419-2425.

An et al.; "Biological Repair of Intervertebral Disc"; SPINE, 2003, vol. 28, No. 15S; pp. S86-S92.

An et al.; "Intradiscal Administration of Osteogenic Protein-1 Increases . . . " SPINE, vol. 30, No. 1, pp. 25-32, 2004.

Ben-Yishay; News & Highlights—IDET—a new procedure for discogenic back pain; http://www.neurospinewi.com/newsletters/IDET.html; printed Dec. 22, 2004; 3 pages.

De Mattei et al.; "Effects of Pulsed Electromagnetic Fields on Human Articular Chondrocyte Proliferation"; Connect Tissue Res., 2001, vol. 42, No. 4, pp. 269-279.

Ganey et al.; "Disc Chondrocyte Transplantation in a Canine Model: A Treatment for Degenerated or Damaged Intervertebral Disc"; SPINE, 2003, vol. 28, No. 23; pp. 2609-2620.

Gruber et al., "Biologic Strategies for the Therapy of Intervertebral Disc Degeneration"; Expert Opinion on Biological Therapy, 2003, vol. 3, No. 8, pp. 1209-1214.

IDET Procedure; http://www.thepainrelief.com/idet_idet.shtml; printed Dec. 22, 2004; 2 pages.

Intradiscal Electrothermal Therapy; http://www.emedicine.com/neuro/topic707.htm; printed Dec. 22, 2004; 8 pages.

Mathews et al.; "Treatment of mechanical and chemical lumbar discopathy by dextrose 25%"; J Minim Invasive Spinal Tech, vol. 1, Inaugural 2001; pp. 58-61.

O'Neill et al.; "Percutaneous Plasma Decompression Alters Cytokine Expression in Injured Porcine Intervertebral Discs"; Spine J., 2004, vol. 4, No. 1, pp. 88-98.

SpineCath Intradiscal Electrothermal Therapy; http://www.spineuniverse.com/displayarticle.php/article217.html; printed Dec. 22, 2004; 3 pages.

Walsh et al.; "In Vivo Growth Factor Treatment of Degenerated Intervertebral Discs"; SPINE, vol. 29, No. 2, pp. 156-163, 2004.

Wang et al.; "Up-regulation of Chondrocyte Matrix Genes and Products by Electric Fields"; Clinical Ortho. & Related Research; Oct. 2004, 427S: S163-S173.

Yoon et al.; "The Effect of Bone Morphogenetic Protein-2 on Rat Intervertebral Disc Cells in Vitro"; SPINE, vol. 28, No. 16, pp. 1773-1780, 2003.

"Pain Management Slnergy System"; Baylis Medical Company Inc., 2006, 2 pages.

International Search Report for International (PCT) Patent Application No. PCT/US06/00312, mailed Jul. 19, 2006.

Written Opinion for International (PCT) Patent Application No. PCT/US06/00312, mailed Jul. 19, 2006.

Supplementary European Search Report for European Patent Application No. 06717501, mailed Mar. 31, 2008.

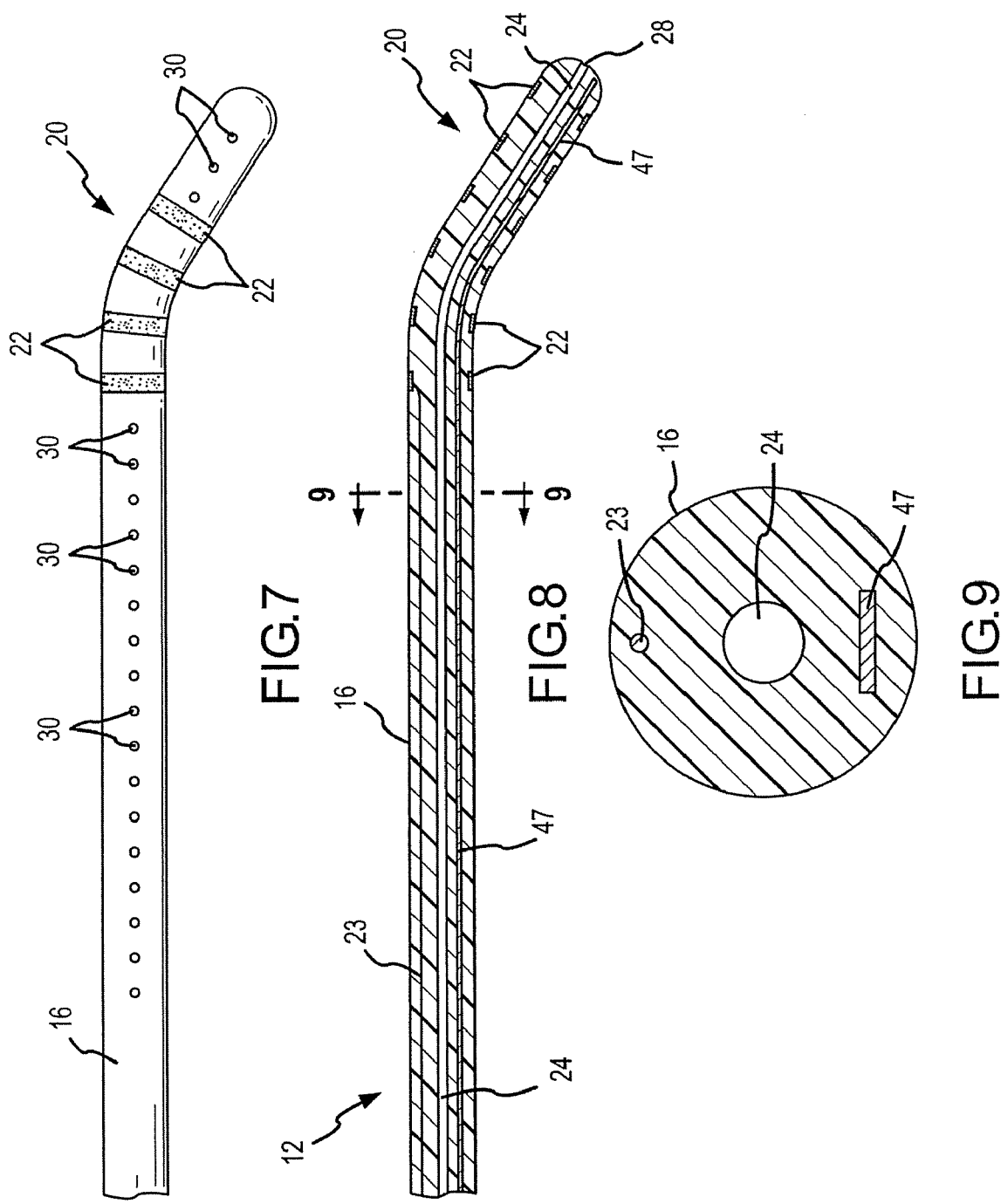

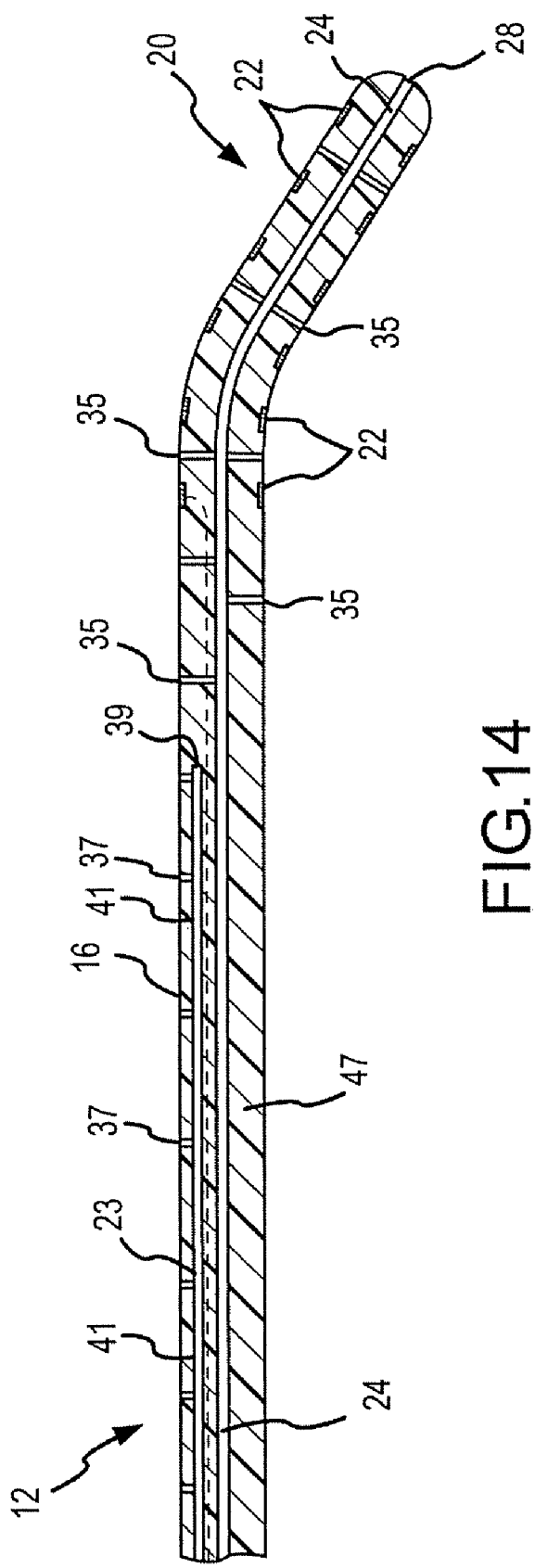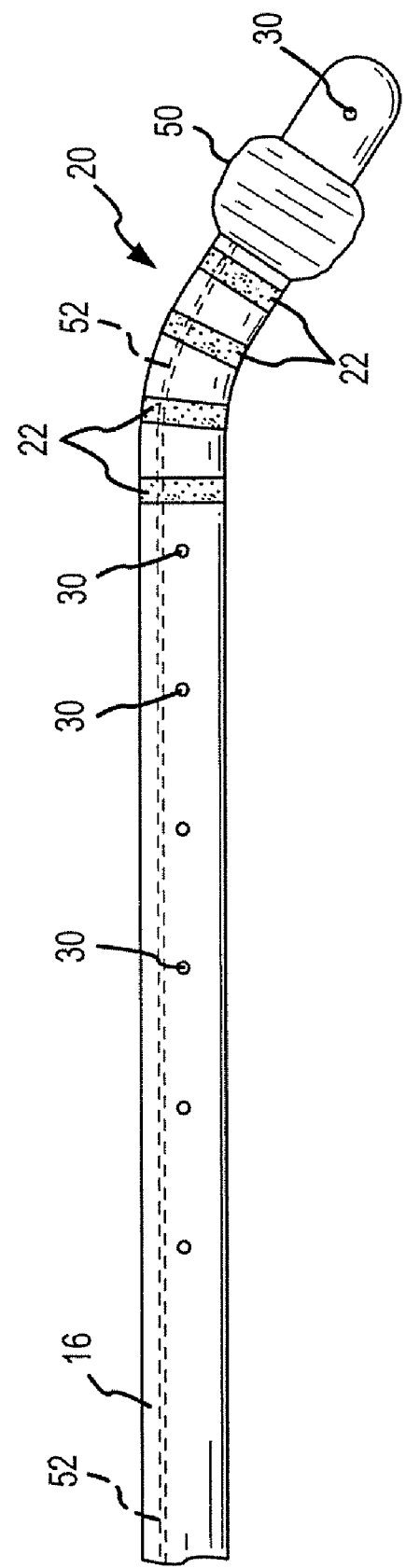
FIG. 14
FIG. 15

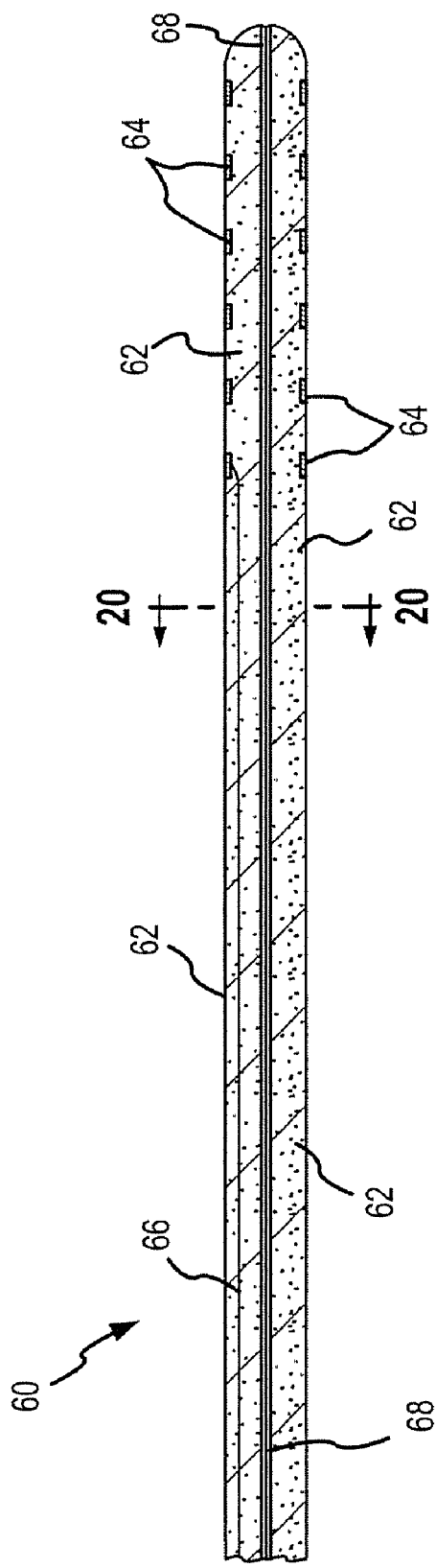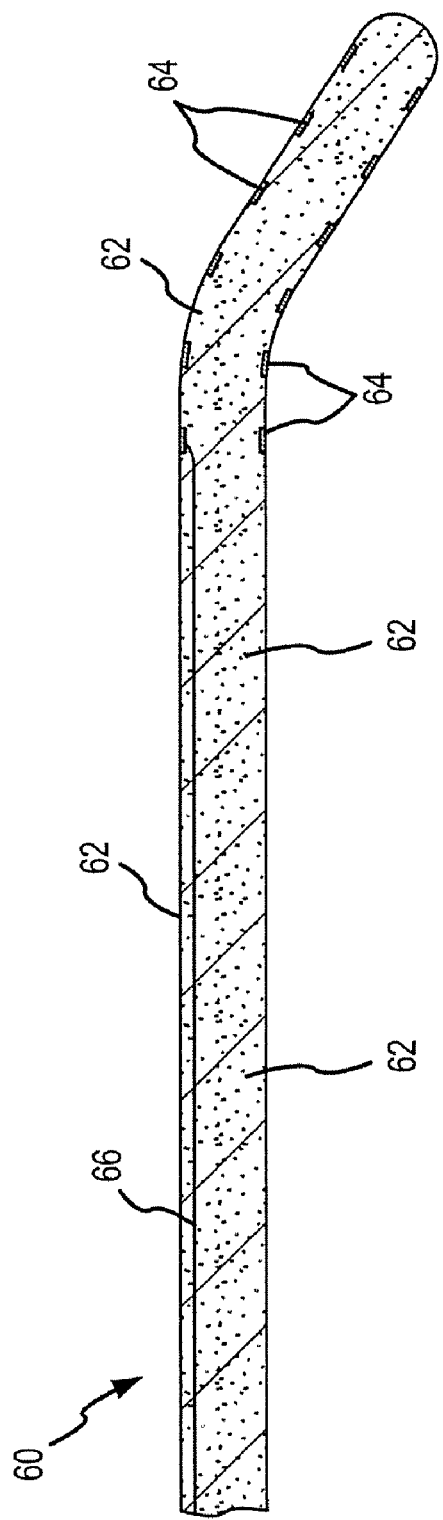
FIG.18
FIG.19

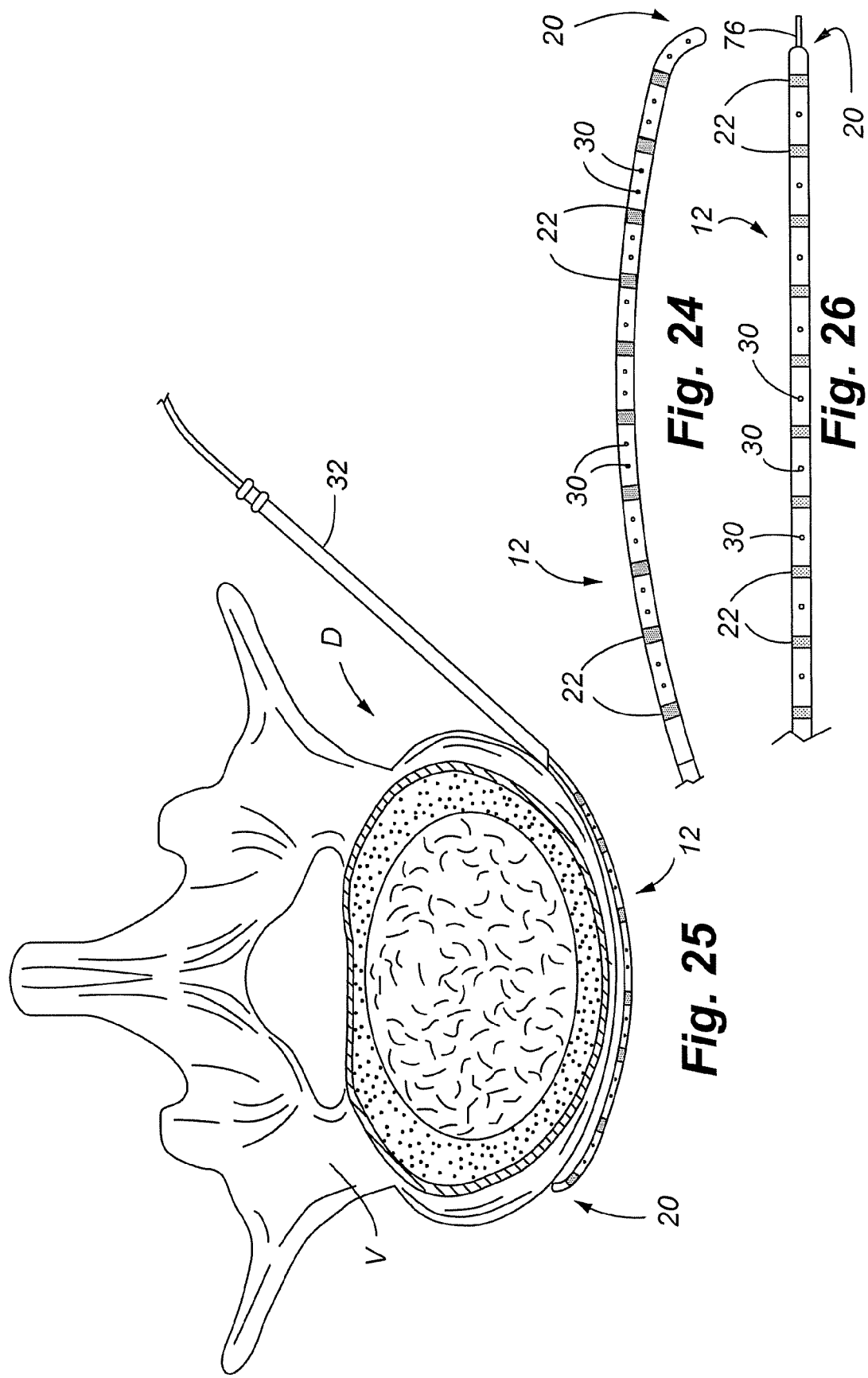

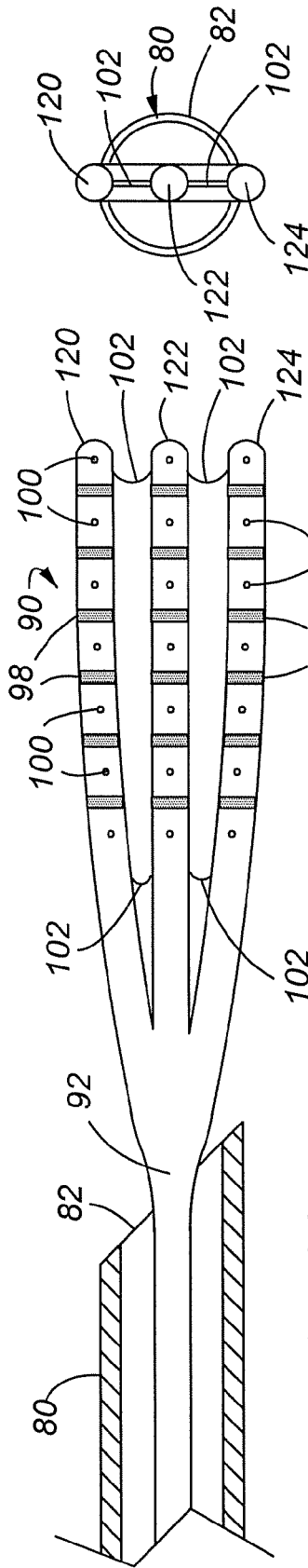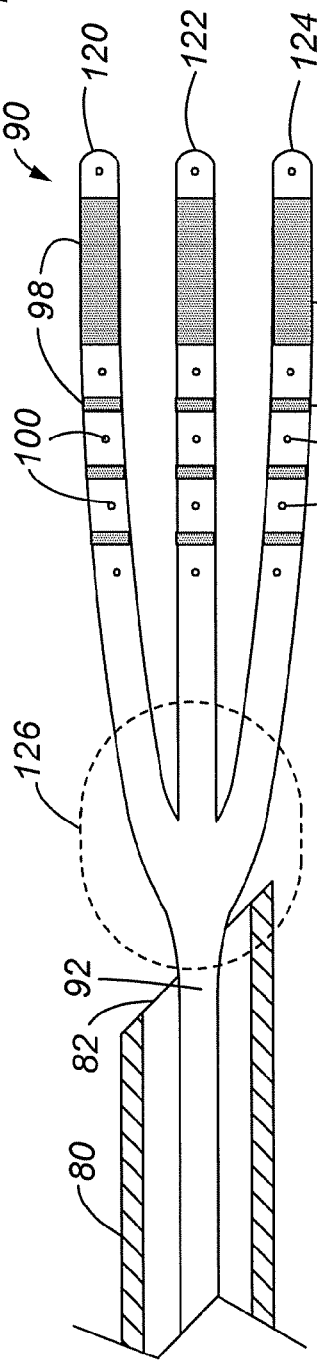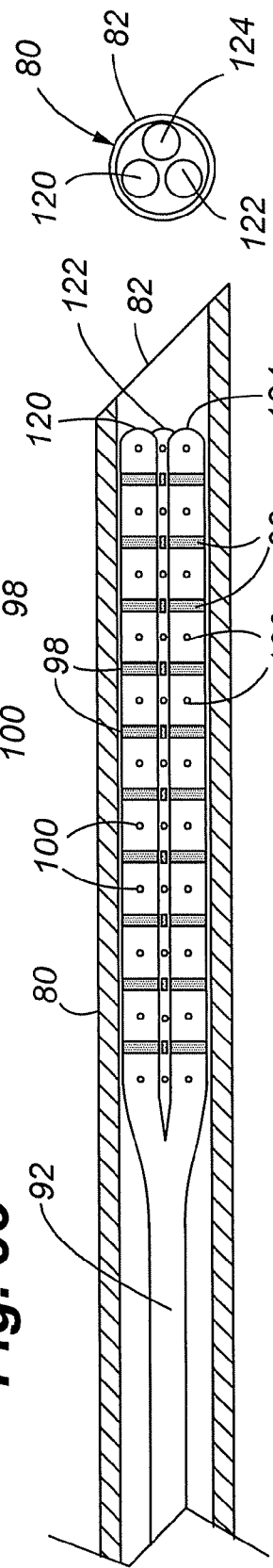
Fig. 33  Fig. 34  Fig. 35  Fig. 36  Fig. 37

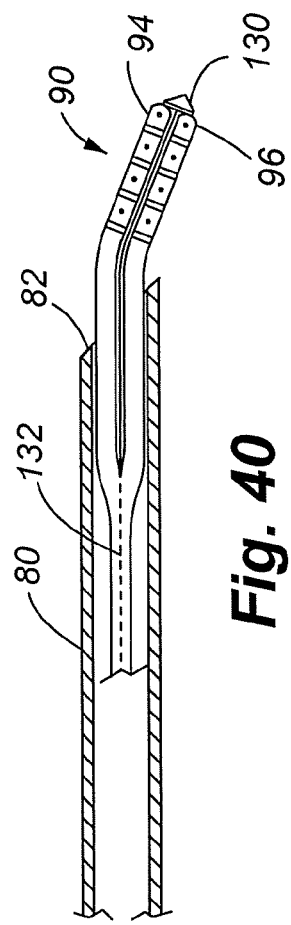
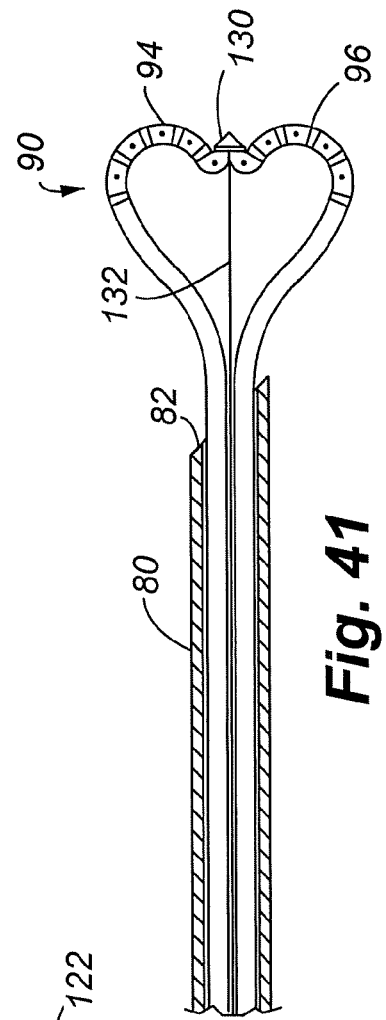
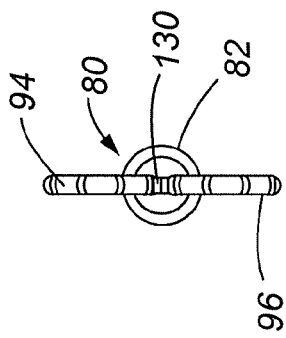
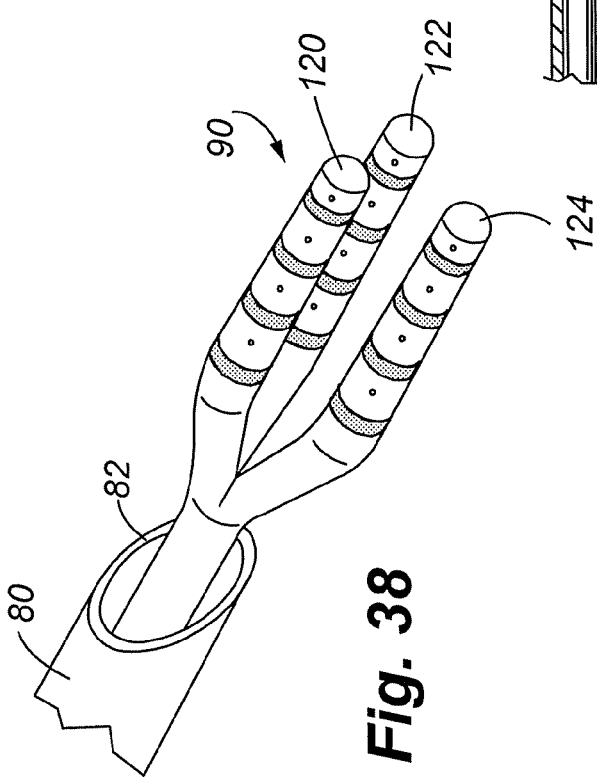
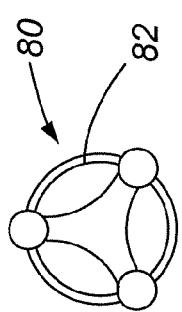

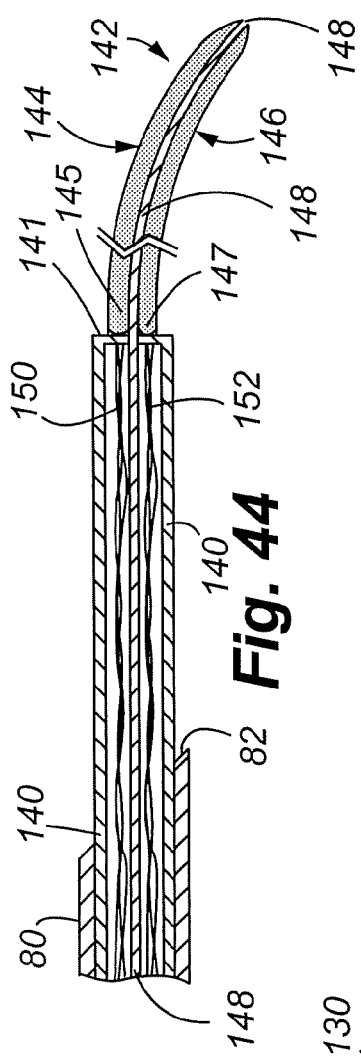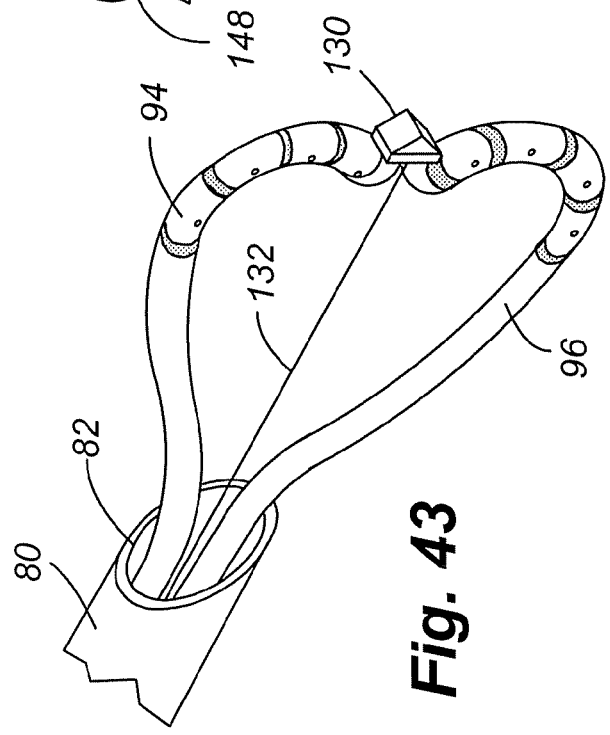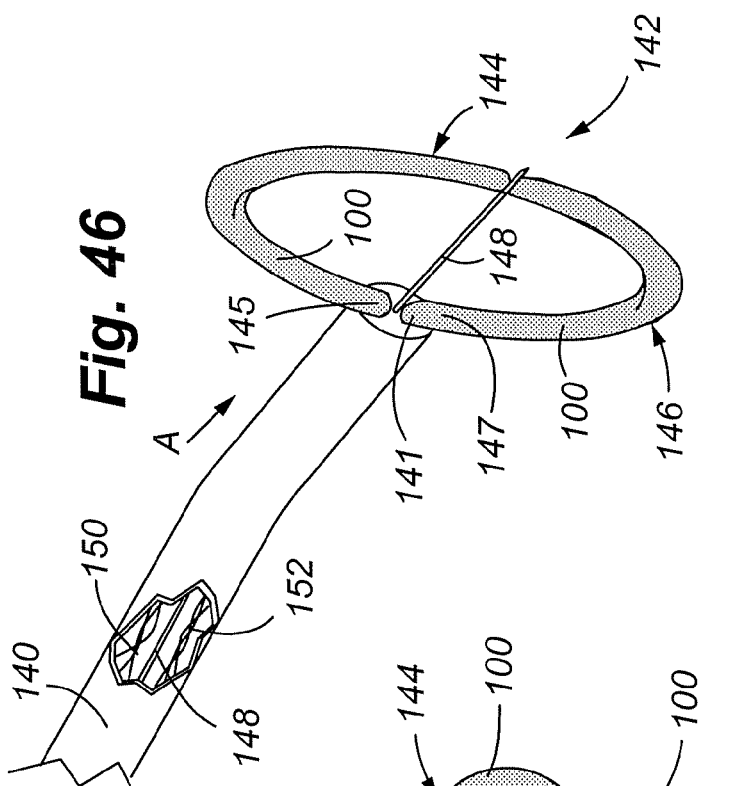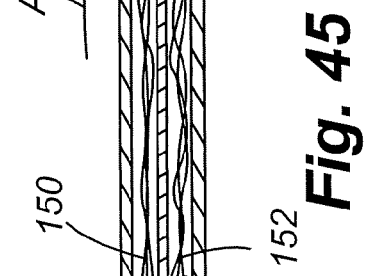

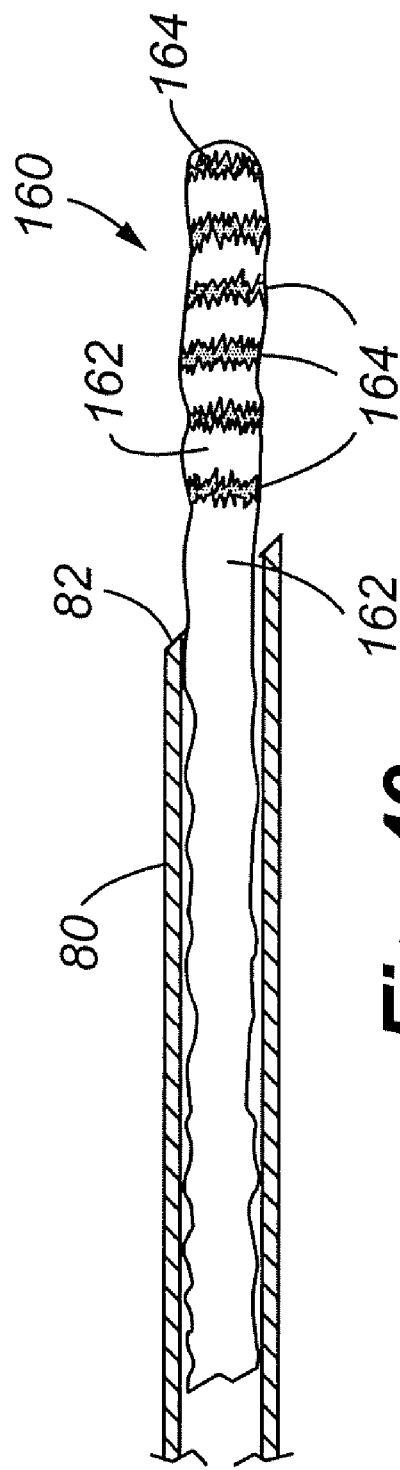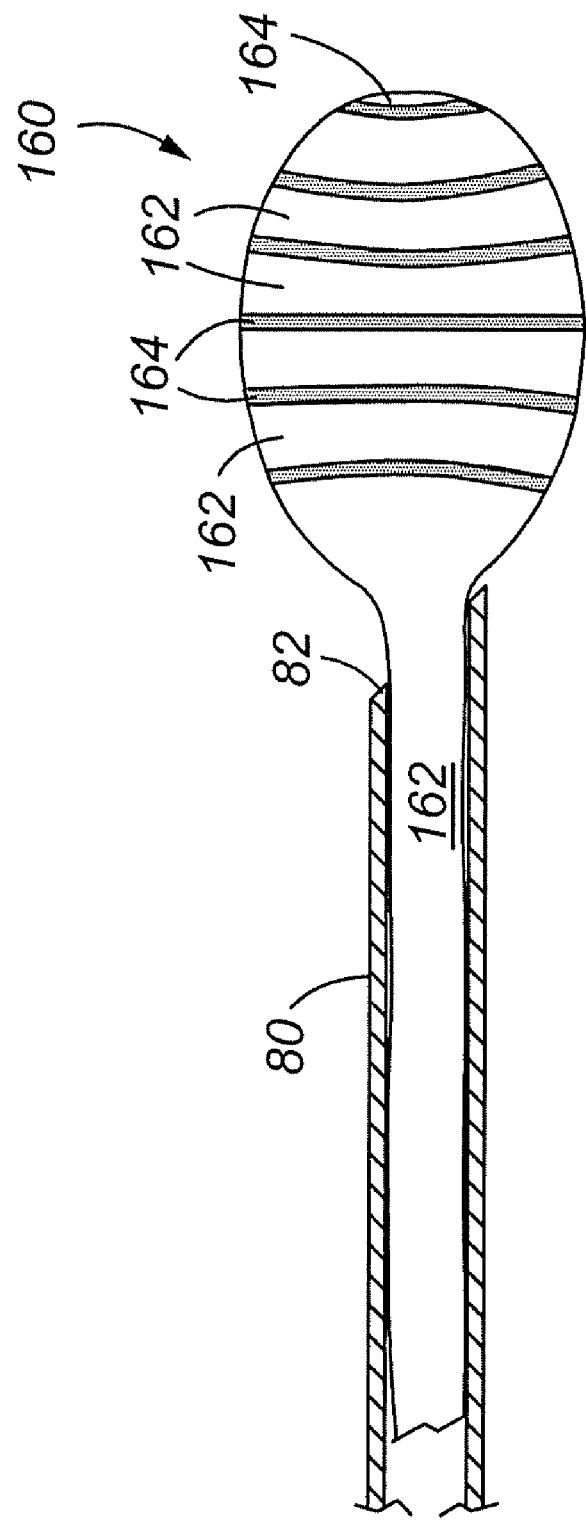
Fig. 49
Fig. 50

COMBINATION ELECTRICAL STIMULATING AND INFUSION MEDICAL DEVICE AND METHOD

CROSS REFERENCE TO RELATED APPLICATION

This application is a continuation-in-part of application Ser. No. 11/107,553, filed on Apr. 14, 2005, entitled "COMBINATION ELECTRICAL STIMULATING AND INFUSION MEDICAL DEVICE", now abandoned, which is a continuation-in-part of application Ser. No. 11/033,591, filed on Jan. 11, 2005, entitled "COMBINATION ELECTRICAL STIMULATING AND INFUSION MEDICAL DEVICE", now issued as U.S. Pat. No. 7,386,350, the disclosures of which are hereby incorporated by reference herein.

TECHNICAL FIELD OF THE INVENTION

The present invention relates generally to electrical stimulation leads and chemical infusion catheters for treatment of medical conditions, and more particularly, to a system, method and device for providing combined electrical stimulation and chemical/drug infusion for treatment of targeted tissue such as intervertebral discs, SI joints, various vertebral structures, and various nerve groups along the spine to include the spinal cord.

BACKGROUND OF THE INVENTION

It is known that immersing certain cell types within an electrical field will cause these cells to proliferate thus facilitating tissue repair. One known use of an electrical field for such repair is "in bone" stimulators that are implanted in fractures and/or spinal fusions. Another type of treatment has recently been developed for spinal conditions wherein target tissue is stimulated by an electrical lead using radio-frequency energy to induce a thermal lesion in the target tissue. In this type of procedure, the therapeutic benefit is intended to derive from heating the target tissue and not from immersing the tissue in an electric field. Thus, the electrical lead in this treatment is strictly for use in heating the tissue, and there is no therapeutic electrical field generated. Chemical treatment of target tissues has also been developed by use of various types of infusion catheters.

For both electrical and thermal stimulation, an electrical current generator, commonly referred to as a pulse generator, may be used to transmit a pulse of electrical current to an implanted stimulation lead that has been precisely placed to transmit the electrical or thermal energy from the electrodes to the target tissue in order to treat the particular condition. For chemical stimulation, one or more drugs or nutrients are delivered by a pump that transfers a desired quantity and frequency of the drug/nutrient through an infusion port of the catheter to the target tissue. For chemical stimulation as well as electrical/thermal stimulation, implanted pumps and generators can be used to deliver the electrical and chemical stimulation as opposed to transdermal delivery devices. More particularly, implanted pulse generators (IPG) as well as implanted drug dispensers (IDP) are commonly used so that patients do not have to return to a medical facility each time treatment is to be conducted.

The intervertebral disc (IVD) provides separation, shock absorption, and controlled motion between vertebral bodies. The disc is comprised of a central nucleus of a semi-fluid mass of mucoid material, (nucleus pulposus), an outer more dense collagen ring (annulus fibrosis), and a thin, metabolically active cellular layer separating the nucleus and the outer collagen ring, referred to as the annular nuclear interface/transitional zone. Disc nutrition is tenuous at best and is provided by diffusion through the vertebral end plate in contact with the outer surface of the disc. As a result, a disc has limited ability to heal or regenerate. Due to age, injury or other conditions, cracks or fissures may develop in the wall of invertebral discs causing a chronic source of pain in many patients. Additionally, the inner disc tissue (nucleus) will frequently cause the disc to bulge or herniate into the fissures in the outer region of the disc, thus causing nerve tissue therein to generate pain signals.

Current treatment for such disc disorders include analgesics, physical therapy and epidural steroid injections. Success with these treatments is frequently disappointing and the patient will all too often have to undergo spinal fusion. Spinal fusion is a very invasive, bio-mechanically altering, and marginally effective treatment.

One relatively new procedure has been developed to treat such disc ailments and general discogenic back pain. As an alternative to other surgical procedures for patients who suffer from back pain caused by certain types of disc disorders, this new procedure is made possible by use of thermal stimulation leads that provide precise temperature control in the delivery of thermal energy to target tissue. This procedure, commonly referred to as intradiscal electrothermal annuloplasty (IDET) was initially believed to function by cauterizing nerve endings within the disc wall to assist in reduction of pain, and the heat produced by the stimulation leads would also thicken the collagen of the disc wall thereby promoting healing of the damaged disc. IDET has proven in some cases to be a minimally invasive procedure to treat these types of disc ailments. However, recent research, and clinical experience has cast doubt as to the exact method of action. More specifically, for percutaneous treatments like IDET, the general operating premise in these procedures, is to heat, either through conduction or induction, causing collagen restructuring and nociceptor coagulation within the disc that would stabilize the structure, and dennervate the painful discs while retaining the motion segment and thus reduce the need for fusion. While these procedures have proven more effective than placebo, the results are far from acceptable. Research has demonstrated that collagen modulation and nociceptor coagulation is unlikely to be the mechanism of action, and that these devices may simply create injury patterns, that in a small subset of patients, stimulates a regenerative response, thereby accounting for the better than placebo results.

Combination electrical stimulators and chemical infusion catheters are known for purposes of treating various spine and brain ailments. One reference that discloses such a combination device is the invention in U.S. Publication No. US2004/0243206. This reference specifically discloses a combination electrical and stimulation lead for stimulation of a person's nerve tissue in the brain. One or more electrodes are located along the lead body and are adapted to be positioned proximate the target nerve tissue and to deliver electrical stimulation pulses transmitted through the lead to the target nerve tissue. One or more infusion ports located along the lead body are adapted for placement proximate the target nerve tissue and to deliver chemical stimulation pulses transmitted through the lead to the target nerve tissue.

While combination electrical and stimulation leads may be known, special considerations must be made for use of such devices for intervertebral disc treatment.

Placement of a stimulation lead within a disc can be quite difficult. Because a disc does not have a uniform density, known stimulation leads can be quite difficult to place and may require the attending physician to make multiple attempts for proper placement or abandon the procedure. Of course, multiple placement attempts greatly increase the invasive nature of the procedure and therefore create unnecessary tissue damage and increased risk. Inability to perform the procedure denies the patient a therapeutic option. Improper placement of the stimulation lead can also result in the undesirable damage of nerve tissue that is not contributing to the chronic pain or other ailments. Because of the overall metabolically inactive nature of the disc, it is also important that chemical infusion be precisely targeted to contact the damaged area of the disc with the delivered chemicals/nutrients, otherwise inaccurate delivery to non-damaged portions of the disc can reduce the effectiveness of the procedure. Thus, there is a need for a combination electrical and chemical stimulation lead that can be precisely placed with a high rate of success on a first attempt.

The IVD is also a motion segment of the body that is subjected to many flexion/extension/rotation cycles every day. In some procedures, it may be necessary to keep the stimulation lead emplaced for long periods of time, such as weeks or perhaps months. Thus, it is desirable to have a stimulation lead that maintains a small profile, yet is resilient enough to withstand the risk of permanent deformation or shearing during treatment and removal of the stimulation lead after treatment.

Many complaints of lower back and leg pain have been attributed to herniated disk related injuries to the spinal column. Extensive therapy and treatment is often unsuccessful in alleviating such pain since some of these problems are actually associated with symptomatic sacroiliac dysfunction or instability. Other terms to describe sacroiliac ailments include sacroiliac joint complex, sacroiliac joint dysfunction, and others. One reference that discloses the use of a bone implant to provide stability and compression for immobilization of the SI joint is the U.S. Pat. No. 6,053,916. One reference that discloses methods for treatment of pain caused by an SI joint dysfunction includes US Pat. App. Publication No. US 2006/0217705. This reference discloses a number of electro-surgical devices in which energy is directed to a targeted region of tissue. A probe is inserted into the target site within the sacroiliac region of the patient's body and energy is delivered to the probe. At the location of the probe, the tissue is ablated thereby creating lesions. In the case of contact of the probe with neural tissues, denervation is achieved which therefore can reduce or eliminate pain associated with the particular dysfunction being treated.

With respect to neural ablation to alleviate symptomatic pain associated with numerous types of spine ailments, current stimulation leads are limited in the provision of ablative heat based on the size of the electrodes, their spacing along the lead, and their particular positioning relative to the targeted nerve group. In many instances, it may be necessary to move the stimulation lead during a procedure to cover all of the targeted tissue and repeatedly apply electrical energy to the lead. In other circumstances, it may be necessary for the introducer needle to be completely removed and reinserted in an adjacent position to then reposition the stimulation lead in order to cover the targeted tissue. Multiple lead position changes during a procedure of course increases the invasive nature of the procedure and also introduces additional risk that multiple needle insertions will damage non-targeted tissue.

While the prior art may disclose various devices and methods for treatment of targeted tissue throughout the body, there is still a need for improved devices and methods for treatment, to include devices and methods wherein electrical stimulation as well as chemical infusion may be provided with the same stimulation device. Additionally, there is a need for an electrical stimulation device that has the capability to provide various types of electrical stimulation and ablative patterns thereby increasing the chances that a procedure will be successful since the patterns can be selected to cover targeted tissue based on the condition of the particular patient and the ailment to be treated.

SUMMARY OF THE INVENTION

In accordance with the present invention, a combined electrical and chemical stimulation device is provided that is especially adapted for treatment of various types of ailments associated with the spine and nervous system.

With respect to treatment of an intervertebral disc, the stimulation device is in the form of a stimulation lead designed to be placed in the disc percutaneously through an introducer needle using an extra-pedicular approach; however, micro-surgical or open-surgical techniques may also be utilized. More specifically, the device of the present invention is specifically designed to facilitate placement proximate to the metabolically active cellular, nuclear, annular interface layer by use of one or more selected embodiments including a straight, curved or bent tip, as well as a variable stiffness tip. Selection of one of these embodiments allows the physician to precisely navigate the lead through the nucleus of the disc. In yet another embodiment of the present invention, the stimulation lead may be placed directly into the nuclear annular interface by use of an introducer needle having a bent tip, and use of a stimulation lead having a straight tip that can take a substantially linear path to reach the target tissue.

With respect to treatment of an SI joint, the same type of stimulation device used for treating the intervertebral disc can be used. Generally, the procedure for treatment of the SI joint involves first the placement of an introducer needle along the curvature of the sacrum with the needle tip ultimately advanced to the superior edge of the sacrum lateral to the sacral foramen and medial to the SI joint. The stimulation lead may be then placed through the introducer needle and advanced to the tip of the introducer needle. The introducer needle is then withdrawn along a specified length of the stimulation lead to expose the active number of contacts necessary to denervate the targeted sacral nerve lateral branches.

The structure of the stimulation lead of the present invention in some embodiments is characterized by an elongate and tubular shaped body including one or more electrodes located along selected portions of the lead body and adapted for positioning proximate the target tissue to deliver electrical stimulation pulses transmitted through the lead. In some embodiments, the electrodes extend circumferentially around a selected length or portion of the lead since it is difficult to orient a specific lateral side of the lead against target tissue. One or more infusion ports may also be located along the lead body and are adapted to be positioned proximate the target tissue to deliver selected chemicals/nutrients. In other embodiments, one large continuous electrode may cover the entire distal portion of the stimulation lead, and this type of lead is especially adapted for ablation procedures.

In some embodiments of the present invention, instead of a single tubular shaped body, the stimulation lead may have a plurality of lead elements with a common base, and the stimulation elements may be selectively deployed at the targeted tissue site. The separate stimulation elements may be deployed by a number of deployment mechanisms to include spring elements, hydraulic force, and selected materials with elastomeric and resilient characteristics that expand the lead elements in the desired configuration once it is freed from within an introducer needle or sheath. In yet other embodiments of the present invention, the stimulation elements may be flat or planar as opposed to tubular shaped. In some of the embodiments, a central stylet can be used to help guide the stimulation lead and to provide some additional rigidity to prevent inadvertent buckling or displacement of the lead.

Once the stimulation lead is correctly positioned, the lead is then connected to a pulse generator for delivery of electrical energy to the electrodes located on the distal portion of the stimulation lead. The electrical circuit can be completed by either use of a grounding pad placed on the patient or by the stimulation lead itself where the electrodes are provided in various combinations of anodes and cathodes. For those embodiments that include infusion ports, the lead may also be connected to an infusion pump that provides a controlled delivery of chemicals/nutrients through the lead to the target tissue. Preferably, the electrical pulse generator and infusion pump are implanted medical devices. These pulse generator and infusion pump devices are also preferably rechargeable and refillable. Another generally desirable characteristic of pulse generators includes those having a capability to produce either constant or variable current. It is also desirable to provide electrical contacts/electrodes that are linked in series, parallel, or combinations thereof which allow selective activation of all or a selected group of the electrodes. Other desirable general characteristics for an infusion pump are those pumps which (i) control infusion material at either a constant or variable rate, and at a constant or variable pressure, or constant or variable volume, (ii) provide automatic compensation for varying infusion pressures, and (iii) have anti-back flow capability to prevent backflow of infusion material through the stimulation lead, as well as pressure safety valves to compensate for overpressure situations. Furthermore, the pump, pulse generator and stimulation lead may be coated with an antibacterial coating to decrease the risk of infection. The pulse generator and pump may also incorporate appropriate alarms to notify of infusion and stimulation failure/abnormality.

Particular embodiments of the present invention provide one or more advantages in terms of navigation of the stimulation lead, as well as placement of the infusion ports and electrodes for effectively delivering electrical and chemical treatment. More specifically, the particular shape of the stimulation lead, as well as the particular placement of the electrodes and infusion ports are especially adapted for delivering the electrical stimulation and chemical infusion to target tissue. A stiffening or support element may be incorporated in the wall of the stimulation lead to ensure the lead does not prematurely shear or otherwise structurally fail during use and removal. The stiffening element is preferably in the form of an elongate support that extends longitudinally within the wall of the stimulation lead and terminating near the distal tip of the lead.

Further advantages and features of the present invention will become apparent from a review of the following detailed description, taken in conjunction with the drawings.

BRIEF DESCRIPTION OF THE DRAWINGS

Reference is now made to the following detailed description taken in conjunction with the accompanying drawings in order for a more thorough understanding of the present invention.

FIGS. 3-7 are greatly enlarged side or elevation views illustrating other preferred embodiments of the stimulation lead;

FIG. 8 is a greatly enlarged cross-section of the working distal portion of another preferred embodiment that incorporates a stiffening element;

FIG. 9 is a section taken along line 9-9 of FIG. 8;

FIG. 14 illustrates a cross section of a further embodiment of the present invention wherein a dual lumen is provided enabling greater selective control of infusion through designated portions of the stimulation lead;

FIG. 15 illustrates yet a further embodiment of the present invention wherein an inflatable member is provided near the distal end of the stimulation lead to help anchor the lead after emplacement;

FIG. 18 illustrates a cross section of yet a further embodiment of the present invention wherein the body of the stimulation lead is made from a dissolvable matrix with the stimulating electrical contacts embedded therein;

FIG. 19 illustrates a cross section of a further variation of the embodiment of FIG. 18 wherein the stimulation lead has a preconfigured bend at the distal end thereof and no central lumen;

FIG. 24 illustrates yet another preferred embodiment of the present invention showing a stimulation lead having a substantially uniform curvature along the length of the stimulation lead along with a bent distal tip;

FIG. 25 illustrates the embodiment of FIG. 24 wherein the stimulation lead is inserted adjacent a selected vertebral structure, for conducting treatment such as ablation of a ventral nerve group;

FIG. 26 illustrates yet another preferred embodiment of the present invention wherein the stimulation lead is substantially liner or straight, and a central needle or stylet is passed through a central lumen of the stimulation lead;

FIG. 33 illustrates yet another preferred embodiment of the present invention having three stimulation elements arranged in a planer or side-by-side fashion.

FIG. 34 is an end view of stimulation lead of FIG. 33 illustrating the planer or side-by-side arrangement of the stimulation elements.

FIG. 35 illustrates yet another embodiment similar to the embodiment of FIG. 33, but the stimulation elements are deployed by the elastomeric force of the stimulation lead material and a different pattern of electrodes and infusion ports are provided;

FIG. 36 illustrates the manner in which the embodiments of FIGS. 33 and 35 may be stored within the introducer needle prior to deployment;

FIG. 37 is an end view of FIG. 36 illustrating the stimulation lead within the introducer needle prior to deployment;

FIG. 38 illustrates yet another embodiment of the present invention wherein the stimulation lead includes three stimulation elements spaced from one another in a triangular configuration;

FIG. 39 is an end view of the embodiment of FIG. 38 illustrating the particular arrangement of the stimulation elements;

FIG. 40 illustrates yet another embodiment of the present invention comprising a pair of stimulation elements that are deployed by a deploying tether;

FIG. 41 illustrates the embodiment of FIG. 40 showing the stimulation elements deployed by retraction of the deploying tether;

FIG. 42 is an end view of FIG. 41;

FIG. 43 is a perspective view of the embodiment of FIG. 40, also illustrating the stimulation elements deployed;

FIG. 44 illustrates yet another preferred embodiment of the present invention comprising a pair of deployable stimulation elements deployed by a movable sheath;

FIG. 45 illustrates the embodiment of FIG. 44 showing the stimulation elements partially deployed;

FIG. 46 is a perspective view of the embodiment of FIG. 44 showing the stimulation elements fully deployed;

FIG. 49 illustrates yet another embodiment of the present invention wherein the stimulation lead is inflatable; and FIG. 50 illustrates the embodiment of FIG. 49 wherein the stimulation lead has been inflated.

DETAILED DESCRIPTION

Figure 1:
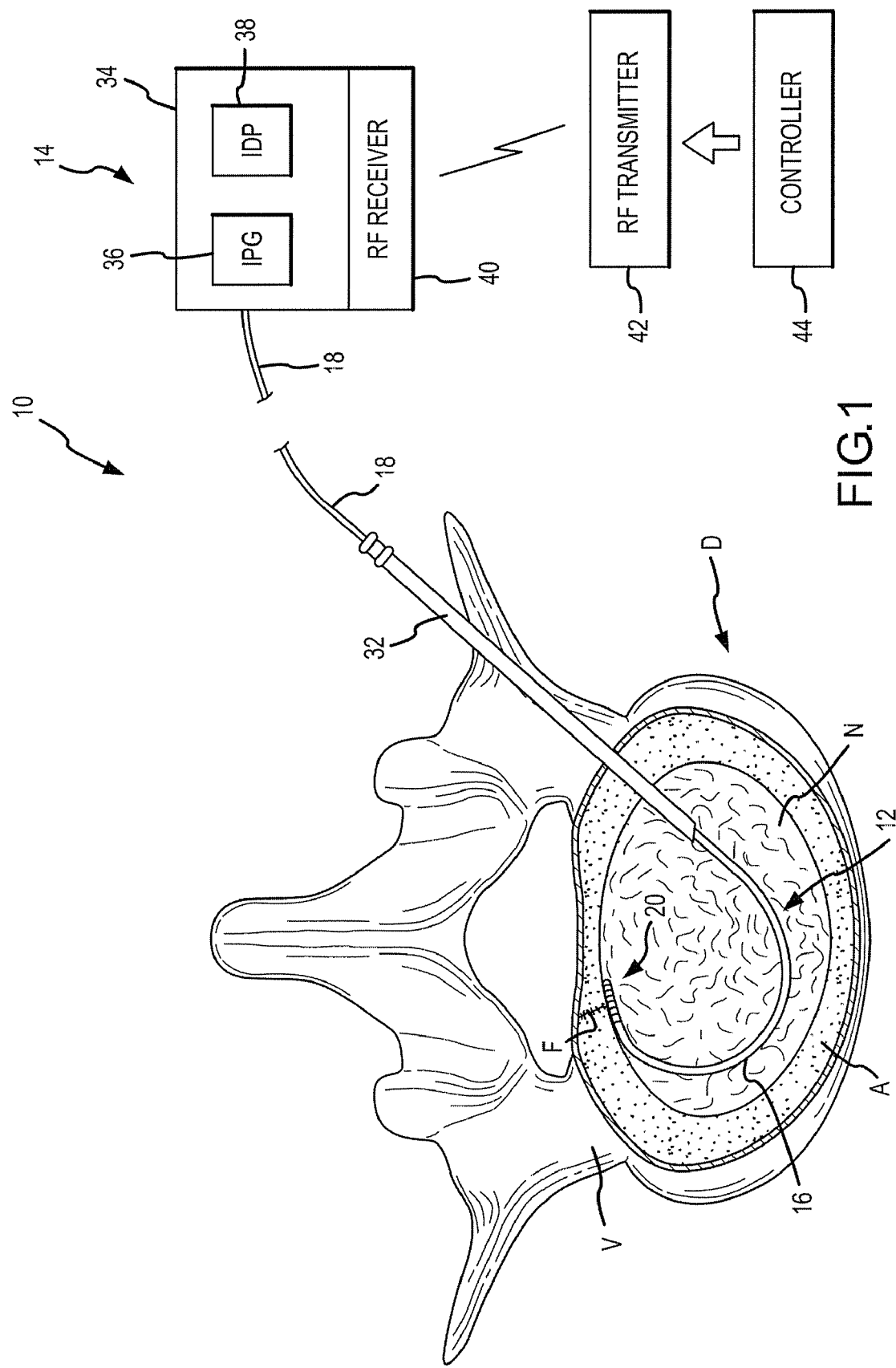
FIG. 1 illustrates the present invention including a stimulation lead inserted in an intervertebral disc, and a stimulation source that provides a controlled delivery of electrical field energy and chemicals/nutrients through the stimulation lead.
Figure 2:
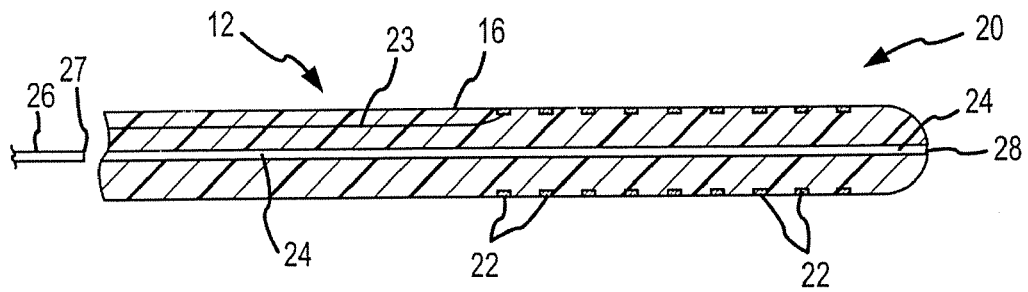
FIG. 2 is a greatly enlarged cross-section of the working distal portion of one preferred embodiment of the stimulation lead of the present invention.

Referring to FIGS. 1 and 2, the system 10 of the present invention is shown that includes a combination electrical and chemical stimulation device 12, a stimulation source 14 that communicates with the stimulation device 12 for delivering electrical energy and chemicals to the stimulation device, and an interventional device such as an introducer needle 32 that allows introduction of the stimulation lead. The stimulation device 12 is shown as inserted within an intervertebral disc D. The combination device 12 more particularly includes a percutaneous electrical and chemical stimulation lead 16 in the form of an elongate tubular member having a desired length and diameter allowing the lead 16 to be placed within the intervertebral disc of the patient to be treated. The working distal portion 20 of the stimulation lead 16 provides the desired stimulation through a plurality of electrodes 22 which are selectively positioned on the distal portion 20, along with a plurality of infusion ports 30 which allow delivery of chemicals/nutrients to target tissue. The proximal portion of the stimulation device 12 can be referred to as a lead extension 18 that connects to the stimulation source 14. The lead extension 18 can be made of the same type and diameter material as the stimulation lead 16, or may be made of a different type of material and diameter.

Referring specifically to FIG. 2, in a first embodiment of the stimulation lead, a plurality of circumferentially extending electrodes 22 are positioned at the distal portion 20. The electrodes 22 are also spaced longitudinally along the distal portion 20. The electrodes produce an array of electrical field energy, and the target tissue is immersed in the electrical field. One or more electrical conductors 23 extend through the interior of the stimulation lead 16 in order to transmit the electrical impulses to the electrodes 22. It is preferable to utilize a single conductor 23 along the major length of the lead, and then provide branch conductors (not shown) at the distal portion 20 that then extend to contact the various electrodes. The branch conductors could be a linearly arranged set of wire extensions extending between each electrode, or any other advantageous combination of wire conductors to interconnect the electrodes. Use of a single conductor is a more robust design as opposed to multiple smaller conductors that are more prone to breakage as a result of the motion cycles of the IVD. It is also contemplated that the electrode could be a single electrode wound in a helical pattern about the distal portion 20. Thus in this helical pattern, only one conductor 23 would be required with no additional branch conductors. In order to generate the desired intensity and size electrical field, the electrodes 22 can be disposed on the distal portion in a pattern or arrangement that best suits the electrical field to be generated. For example, in the helical pattern, the electrode could be wound with a tighter pattern to generate a more intense field, while a looser more spaced pattern would generate a less intense field. Of course, the particular signal or impulse current provided to the electrodes also determines the intensity of the field generated.

In order to provide chemical infusion, a central lumen or passageway 24 is formed through the stimulation lead. The central lumen 24 may extend completely through the lead thereby forming a distal opening 28 in the stimulation lead and providing one infusion port that is directed distally of the stimulation lead.

The stimulation lead 16 may be made of a homogeneous material, or may be made of differing materials that cause the stimulation lead to have either a more progressively stiff or more progressively flexible characteristic as the lead extends in the distal direction. Depending upon the manner in which the stimulation lead is to be emplaced, it may be desirable to use either the more progressively stiff or more progressively flexible arrangement.

In accordance with the method of the present invention, a stylet (not shown) is first inserted through the introducer needle 32. The introducer needle 32 is emplaced by penetrating the skin and muscle tissue, and ultimately into the disc D. When the introducer needle has penetrated the disc, the stylet is removed and the stimulation lead 16 is then inserted through the lumen of the introducer needle.

Referring again to FIG. 1, the stimulation lead 16 is illustrated as being emplaced within the disc D. This disc D is shown in cross section along with an adjacent vertebra V. The stimulation lead 16 is shown as taking an arcuate or curved path through the disc nucleus N in order to be precisely positioned at the area of the disc to be treated, illustrated as a fissure F which has developed adjacent the spinal fluid sac (not shown). The other primary features of the disk D are also illustrated including the annulus fibrosis A and the thin layer L defining the annular nuclear interface/transitional zone.

The stimulation source 14 is preferably an implantable medical device 34 including both an IPG (implantable pulse generator) 36 and an IDP (implantable drug dispenser) 38. The implantable device 34 could be contained within a single structural housing, or two separate housings, one for the IPG 36, and one for the IDP 38. The IPG and IDP can both be self-contained devices with internal control for preset delivery of electrical and chemical pulses. Alternatively, an external controller 44 could be used to modify the desired treatment protocol by use of RF transmission wherein an implantable RF receiver 40 is integrated with the IPG 36 and IDP 38. The RF receiver 40 could also be housed within the same implantable medical device 34, or could be a separate implanted device. An external RF transmitter 42 transmits RF signals to control the delivery of electrical stimulation and chemicals to the stimulation lead 16. A controller 44 provides the specific instruction set for transmission by the RF transmitter 42.

In accordance with the apparatus and method of the present invention, there are a number of nutrients and medications that can be delivered by the stimulation lead. For nutrients, this list includes, but is not limited to, glucose, glucosamine, chondroitin, oxygen and oxygenating agents, anti-oxidants, anti-glycosylating agents, and pH buffers. For medications, these may include, without limitation, anti-inflammatory agents and growth factors, such as growth and differentiating factor-5 (GDF-5), transforming growth factor-beta (TGF-β), insulin-like growth factor-1 (IGF-1), and basic fibroblasts growth factor (bFGF). In terms of the types of electrical impulses provided to the electrodes 22, these electrical impulses may be continuous or variable over time, and may vary based upon voltage, amperage, and alternate current frequency.

Figure 3:
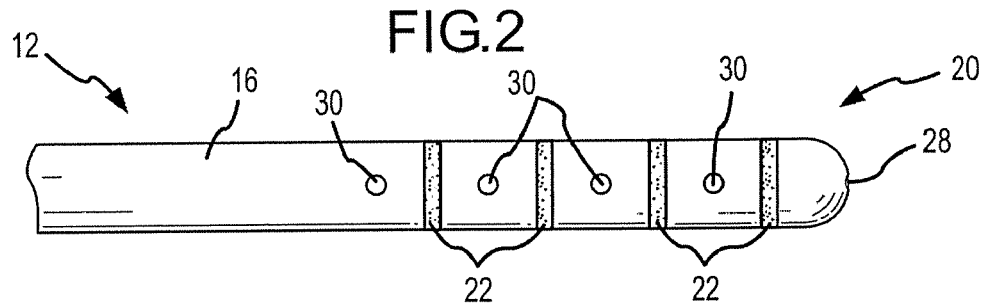

Referring to FIG. 3, a different arrangement is illustrated with respect to the location of the electrodes 22, and the single infusion port at distal opening 28 is supplemented with a plurality of additional infusion ports 30. In this embodiment, fewer electrodes are incorporated, yet additional infusion ports 30 are provided that are spaced longitudinally along the length of the lead 16 and placed between the electrodes 22.

Figure 4:
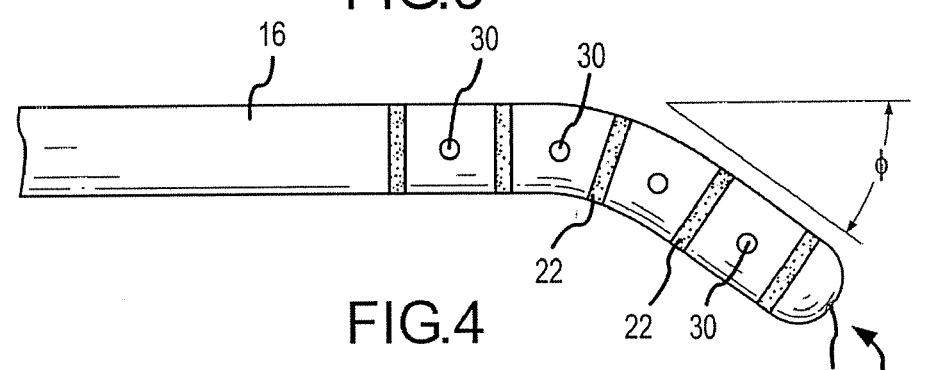

FIG. 4 shows another embodiment with a different arrangement of electrodes 22 and infusion ports 30 as well as a modification of the stimulation lead shape to include a bent distal tip having a chosen bend angle Ø. The bend angle Ø helps define the path of travel of the lead within the disc nucleus during emplacement. In other words, imparting a particular bend angle on the distal tip of the stimulation lead causes the stimulation lead to travel in an arcuate path such as shown in FIG. 1. Imparting a greater bend angle on the lead results in the stimulation lead traveling in a tighter arcuate path, while imparting a lesser bend angle generally results in the stimulation lead traveling in a broader arc or arcuate path.

Figure 5:
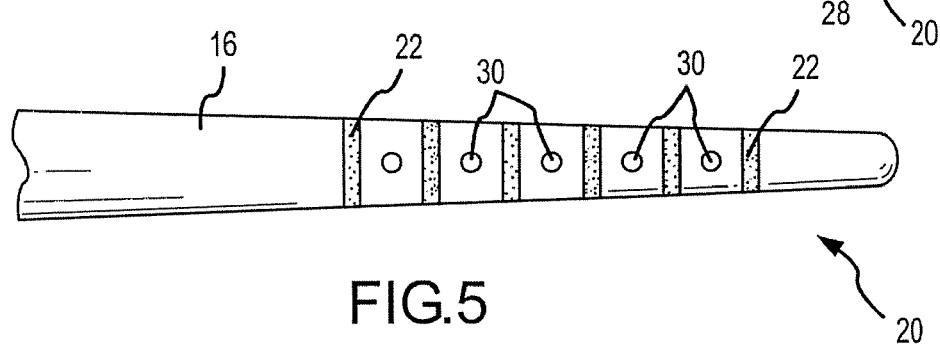

Referring to FIG. 5, another embodiment of the stimulation lead is illustrated wherein the lead has a progressively narrowing diameter towards the distal end thereof. With this type of stimulation lead, travel of the lead through the more dense annulus tissue is facilitated because the distal tip has a smaller frontal profile and is more easily controlled.

Figure 6:
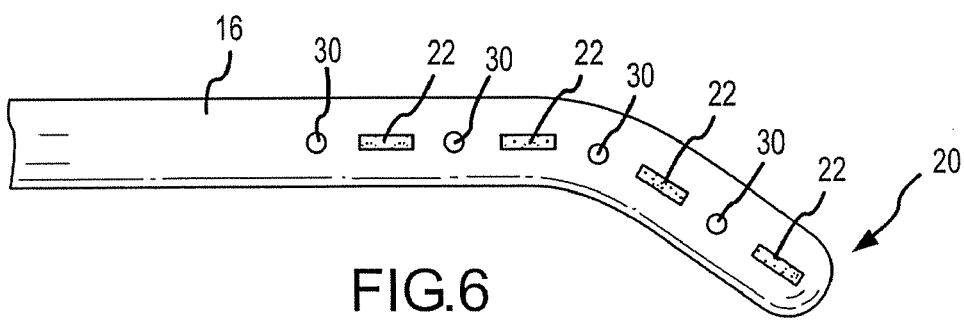

Referring to FIG. 6, yet another embodiment of the stimulation lead is illustrated wherein the electrodes 22 are not formed circumferentially around the distal portion 20, but are formed more linearly along one side of the stimulation lead. Additionally, the infusion ports 30 may have more of an oval shape and be larger in size that facilitates greater volumetric infusion. This embodiment may be preferred when it is desired to more precisely direct the array of electrical energy to the target tissue. The electrical energy array that is created by circumferentially arranged electrodes result in transmission patterns having a radial or circular pattern extending away from the stimulation lead. Thus, a plurality of circumferentially arranged electrodes transmit energy in all directions to tissue that surrounds the stimulation lead. On the contrary, locating the electrodes only along one side or edge of the stimulation lead results in transmission of energy in a more linear and less radial pattern, and directed primarily orthogonal or perpendicular to the axis of the stimulation lead. The embodiment of FIG. 6 also illustrates the distal end as being bent at a desired angle.

FIG. 7 illustrates yet another embodiment of the stimulation lead wherein the electrodes 22 are concentrated at a particular location, and the infusion ports 30 are spaced in a pattern extending a greater longitudinal length of the lead. A stimulation lead in this particular arrangement may be particularly suitable for repair of a fissure located at a very defined position within the disc, yet if the disc shows great overall degeneration, it is preferable to provide nutrients to a greater length of the annulus whereby the infusion ports 30 can distribute nutrients to a greater length of the annulus.

FIG. 8 illustrates yet another preferred embodiment of the present invention wherein a stiffening or strengthening member 47 is incorporated within the structural wall of the stimulation lead to provide increased strength to the lead without enlarging the frontal profile of the lead. As shown, the stiffening member 47 is an elongate member that extends longitudinally through the wall of the lead and terminates near the distal end thereof. The stiffening member is malleable to a degree that allows the lead to maintain some desired flexibility during emplacement, but increases the overall shear and torsional strength of the lead to prevent premature failure after emplacement or during removal. The member 47 could be made of a selected metal or thermoplastic approved for medical use.

Figure 10:
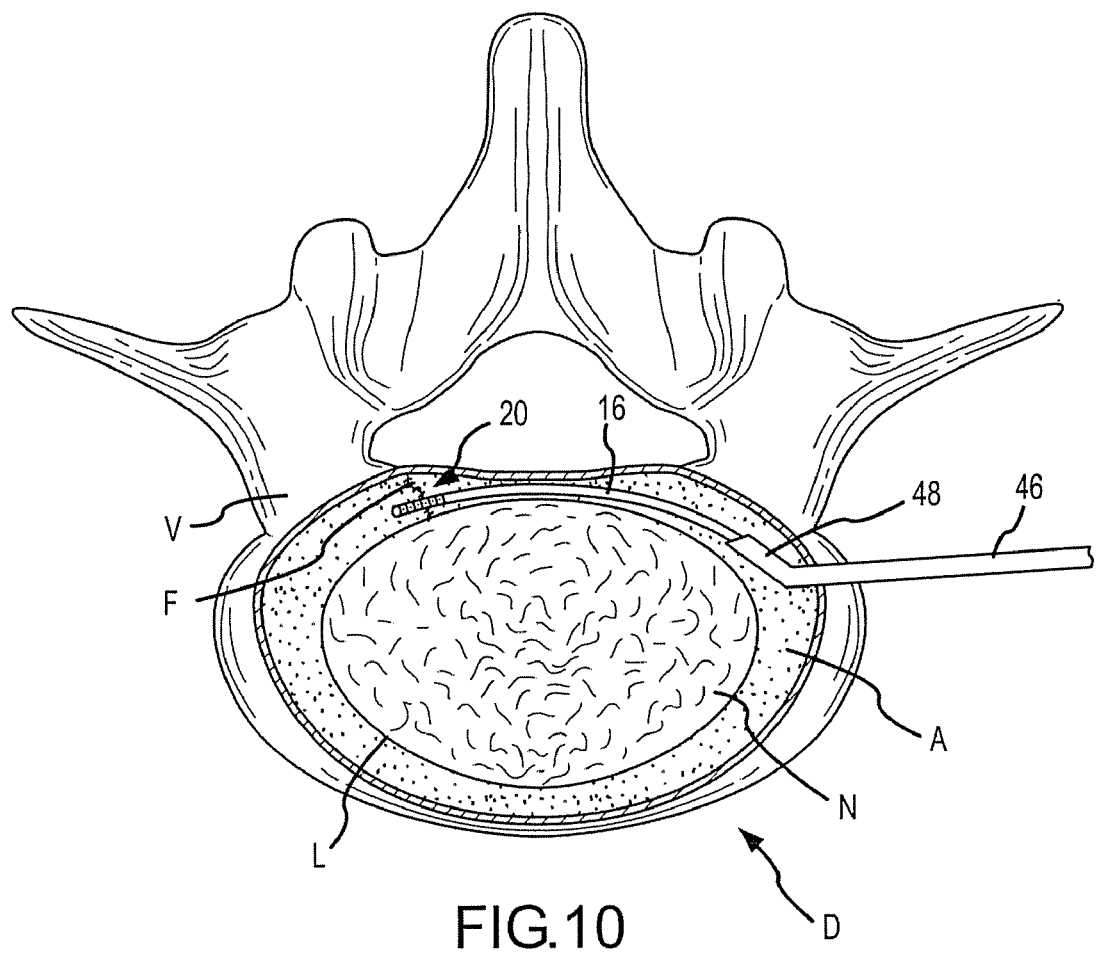
FIG. 10 illustrates another preferred embodiment of the present invention in the form of an introducer needle having a bent distal end for placement of the stimulation lead directly into the nuclear annular interface of an intervertebral disc.

Referring to FIG. 10, yet another embodiment of the invention is shown wherein an introducer needle 46 is not placed within the disc nucleus, but rather is placed only into the disc annulus, and then the stimulation lead 16 extends through the disc annulus to the target tissue, also shown as a fissure F. In this embodiment, it is preferable that the stimulation lead 16 exits the introducer needle through a bent distal portion 48 so that the lead travels in a more parallel fashion within the annulus and along a more linear path to the target tissue. Accordingly, a stimulation lead having a straight tip like shown in FIGS. 2, 3 and 5, would be more suitable according to this embodiment. In the event the distal opening 28 of the lead 16 is of a size which could allow nuclear tissue to clog or block the distal opening 28, a guide wire 26 (see FIG. 12) may be inserted through the lumen 24 of the lead 16, and the distal tip 27 of the guide wire could be placed flush with the distal opening 28 in order to prevent clogging of the distal opening 28, as well as to provide additional rigidity for placement of the stimulation lead 16. If the guide wire 26 is used, then the guide wire 26 is removed prior to connecting the stimulation lead 16 to an IDP and/or IPG. Also, the central lumen may terminate before passing through the distal tip of the lead. Thus, all of the infusion ports 30 would be arranged on the lead to direct chemicals/nutrients in a perpendicular direction away from the axis of the lead.

Figure 11:
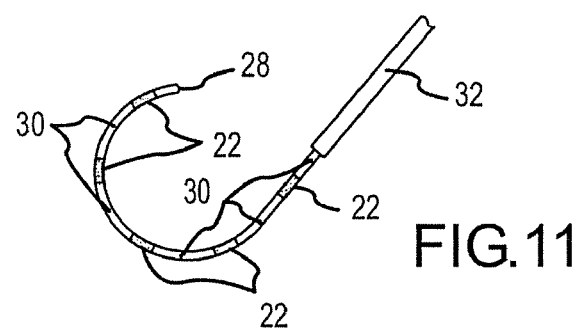
FIGS. 11-13 illustrate further embodiments of the present invention wherein the electrodes and infusion ports are dispersed substantially along the entire length of the stimulation lead.
Figure 12:
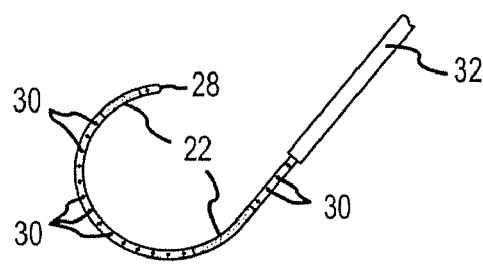
Figure 13:
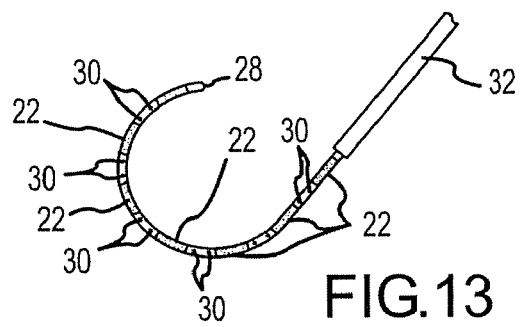

FIGS. 11-13 illustrate yet further embodiments of the present invention wherein the electrodes 22 and infusion ports 30 are dispersed along substantially the entire length of the stimulation lead. In many cases, the disc to be treated has undergone such great degeneration that the entire disc is in need of treatment, as opposed to a more minor degenerative condition such as a single localized fissure. In such cases, it is advantageous to provide both electrical and chemical stimulation to as much of the disc as possible. The embodiments at FIGS. 11-13 show various combinations of the electrodes 22 and ports 30 that provide greater dispersion of the electrical and chemical stimulation. Specifically, the electrodes are larger and are spread out along a greater length of the lead. The infusion ports are also spread out along a greater length of the lead.

FIG. 14 illustrates yet another embodiment of the invention wherein a second lumen 41 is incorporated within the stimulation lead to provide greater infusion selectivity. More specifically, FIG. 14 shows that the second lumen 41 terminates at end 39 which is intermediate between the distal tip of the stimulation lead and the proximal end thereof. This lumen 41 communicates with the set of infusion ports 37 which are spaced from the end 39 of the lumen 41 towards the proximal end of the lead. The first or central lumen 24 then communicates with the infusion ports 35 that are located distally of the end 39 of the second lumen 41.

During treatment, it may be desirable to administer nutrients and/or medications to different parts of the disc being treated. Furthermore, it may be desirable to provide the nutrients/medications to these different locations within the disc at differing flow rates and at differing times and frequencies. With the provision of a dual set of lumens, a physician has the ability to selectively control infusion to two distinct areas within the disc, and can vary the treatment protocol between the two areas of the disc by selecting the particular dosing, frequency, and makeup of the infusion material to the distinct locations within the disc. This selective treatment capability may be advantageous where, for example, the distal end of the stimulation lead may be placed near the interface/transitional zone, and the tissue extending therealong together with the annulus fibrosis may have particular needs in terms of the required type of nutrients and/or medication, while the tissue within the nucleus may have slightly different needs. Thus, the embodiment at FIG. 14 provides the treating physician with additional options in providing effective treatment.

The particular sizes of the lumens, as well as the sizes and spacing of the openings 35 and 37 may be configured for optimal delivery of various types of infusion material. For example, assuming that the desired nutrient/medication to be delivered to the distal end of the stimulation lead was fairly viscous, it may be advantageous to provide the lumen 24 with a larger cross-sectional size, as well as to provide the infusion openings 35 of an increased size to accommodate the higher viscosity. As a further example, if the lumen 41 was to deliver a less viscous nutrient/medication, then the lumen 41 would preferably have a smaller cross-sectional area, and the openings 37 would preferably be smaller than the openings 35. Thus, one convenient way in which to control infusion is to advantageously arrange the particular size, number, and spacing of the infusion openings as well as the size of the lumens which deliver the infusion material through the openings.

It is further contemplated within the present invention to also provide non-uniform lumens, as well as infusion openings that vary in size within the same supplying lumen. As discussed above, the IDP 38 may be programmed for preset delivery of chemical "pulses". The IDP 38 is typically programmed to be in an "on" or "off" state to generate delivery of a set amount of fluid over a specific period of time. However, once the infusion material is released from the IDP, the IDP itself does not have control over the way in which the infusion material is dispersed through the stimulation lead. Assuming that a lumen of a stimulation lead has a uniform diameter with infusion openings also being of a uniform diameter, then the infusion ports located at the more proximal end of the device will most likely deliver a greater amount of material to the disc as opposed to the infusion ports located at the distal end of the device because there will be an inherent loss in the amount of fluid delivered downstream based on frictional losses within the lumen and the upstream openings communicating with the lumen. Therefore, in order to ensure equal distribution of infused material, it may be desirable to provide a lumen having a diameter that progressively enlarges as it extends towards the distal end of the device. Alternatively or in combination with the progressively changing lumen size, it may be desirable to provide infusion ports toward the proximal end of the device that are slightly smaller than the infusion ports located towards the distal end of the device to further help compensate for any frictional line losses.

Referring to FIG. 15, yet another embodiment of the present invention is provided which further includes an inflatable portion 50 in the form of a bladder or balloon that is selectively inflated or deflated by an inflation line 52 extending conterminously with the central lumen. The inflatable portion is mounted to the exterior surface of the stimulation lead, and the inflation line 52 extends through an opening (not shown) in the sidewall of the lead that is covered by the inflatable portion 50. The inflation line 52 communicates with a source of compressed fluid (not shown), and the physician may inflate the inflatable portion 50 to a desired size. As also shown, the inflatable portion 50 is preferably placed along a location of the stimulation lead that does not cover or block any infusion ports 30, as well as any electrodes 22.

Figure 16:
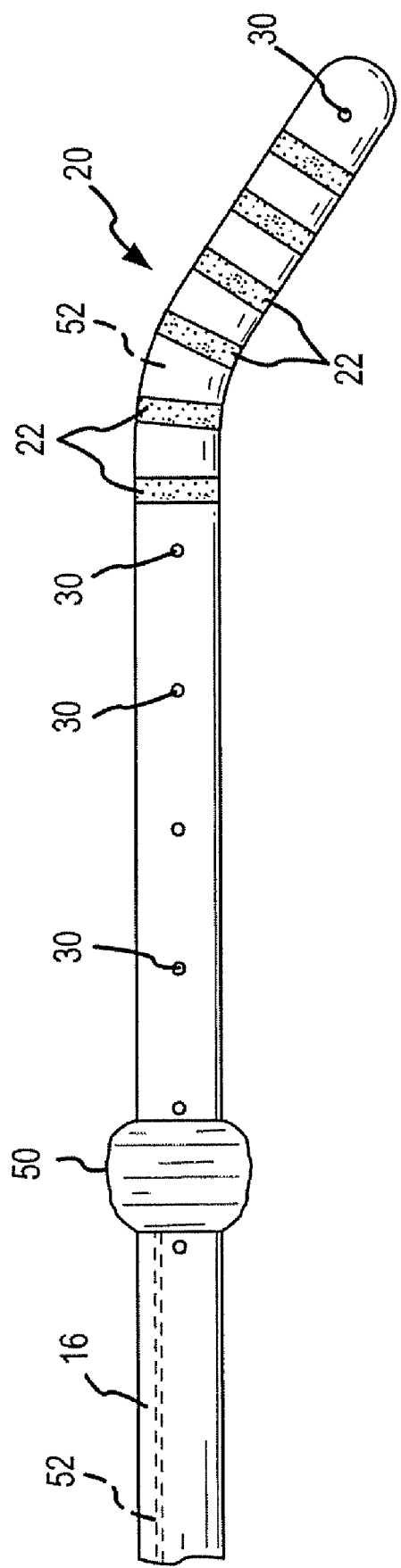
FIG. 16 illustrates the embodiment of FIG. 15 but the inflatable member being provided near the proximal end of the stimulation lead.

In some instances, the stimulation lead may reside within a patient for an extended period of time. As time passes, the stimulation lead may have a tendency to migrate or drift within the disc. Drifting of the stimulation lead can be problematic for a number of reasons, to include causing damage to the disc by penetration of the distal tip of the stimulation lead completely through the disc, as well as drifting of the stimulation lead so that it is no longer centered around/along the desired area of the disc to be treated. To maintain the stimulation lead in its desired position after the stimulation has been emplaced, the inflatable portion 50 may be inflated to the desired size, thereby serving as an anchor to help prevent drifting of the stimulation lead within the disc. In most instances, it is desirable to place the inflatable portion 50 near the distal tip of the stimulation lead to best prevent undesired drift of the stimulation lead; however, it is also contemplated within the present invention that the inflatable portion 50 may be selectively placed along other areas of the stimulation lead to best serve as an anchor. For example, as shown in FIG. 16, the inflatable portion is located at the proximal end of the stimulation lead. Furthermore, it may be desirable to incorporate both a distally located inflation portion 50, and another inflation portion located at the proximal end of the device that would further help to prevent the stimulation lead from drifting or from being inadvertently removed.

Some disc tissue may have a tendency to adhere to a stimulation lead that has been emplaced within the disc for a long period of time, and/or the disc tissue may have a tendency to harden around the emplaced stimulation lead thereby making it more difficult to remove the stimulation lead. Thus, it is also contemplated within the present invention that the inflatable portion 50 could be provided to extend along a much greater distance of the stimulation lead, and the inflatable portion 50 could be inflated to a desired level prior to the stimulation lead being emplaced within a disc. When it is then desired to remove the stimulation lead, the inflatable portion could be deflated which would create a small gap or space between the surrounding disc tissue and the stimulation lead thereby easing removal of the stimulation lead.

Thus, the inflatable portion 50 can be used either as an anchor to maintain positioning of the stimulation lead within the disc, or the inflatable portion 50 can be used in a reverse role by enlarging the overall size of the stimulation lead once emplaced, but then reducing the overall size of the stimulation lead by deflating the inflatable portion when it is desired to remove the stimulation lead.

Figure 17:
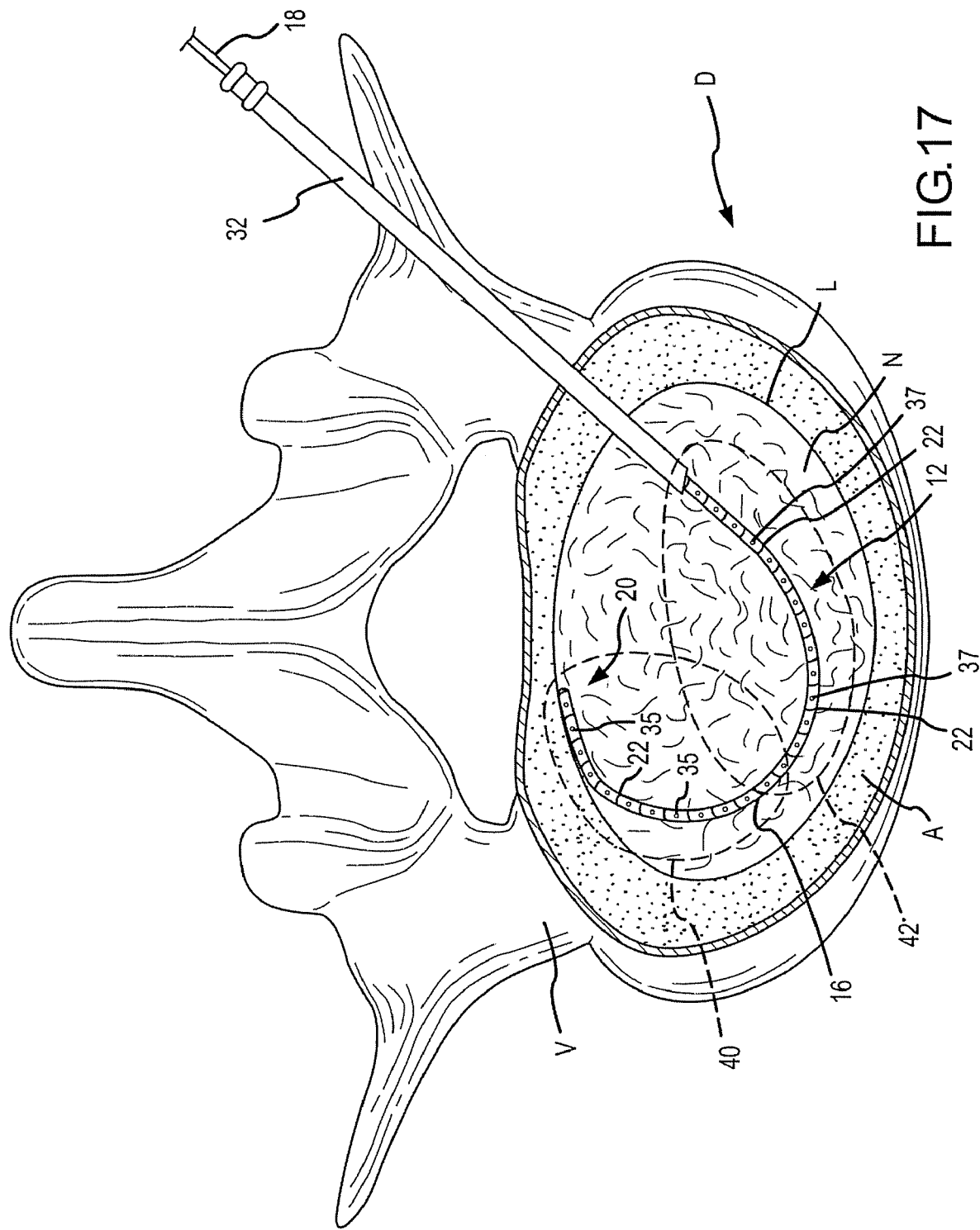
FIG. 17 illustrates the stimulation lead of FIG. 14 inserted in an invertebral disc wherein the lead can selectively treat two targeted treatment zones or areas within the disc.

Referring to FIG. 17, a stimulation lead is shown emplaced within a disc D, the stimulation lead generally corresponding to the embodiment shown in FIG. 14. Two oval shaped areas 40 and 42 are shown surrounding the distal and proximal sections of the stimulation lead, respectively. These areas 40 and 42 may generally represent targeted treatment areas within the disc. In accordance with the embodiment of FIG. 14, the physician has the option of applying different infusion materials through the separate sets of infusion ports 35 and 37 to specifically target the tissue located within the areas 40 and 42. Such treatment could be simultaneous, sequential, or any combination thereof. Furthermore, as mentioned above, selected sets of electrodes could be energized to provide treatment. For example, the electrodes may be wired so that the physician has the ability to energize two primary sets of electrodes, one set providing an electromagnetic field generated to cover area 40, and the other set providing an electromagnetic field to cover area 42. The electrodes may be wired and configured to provide generation of electromagnetic fields in any desired pattern along the length of the lead.

Figure 20:
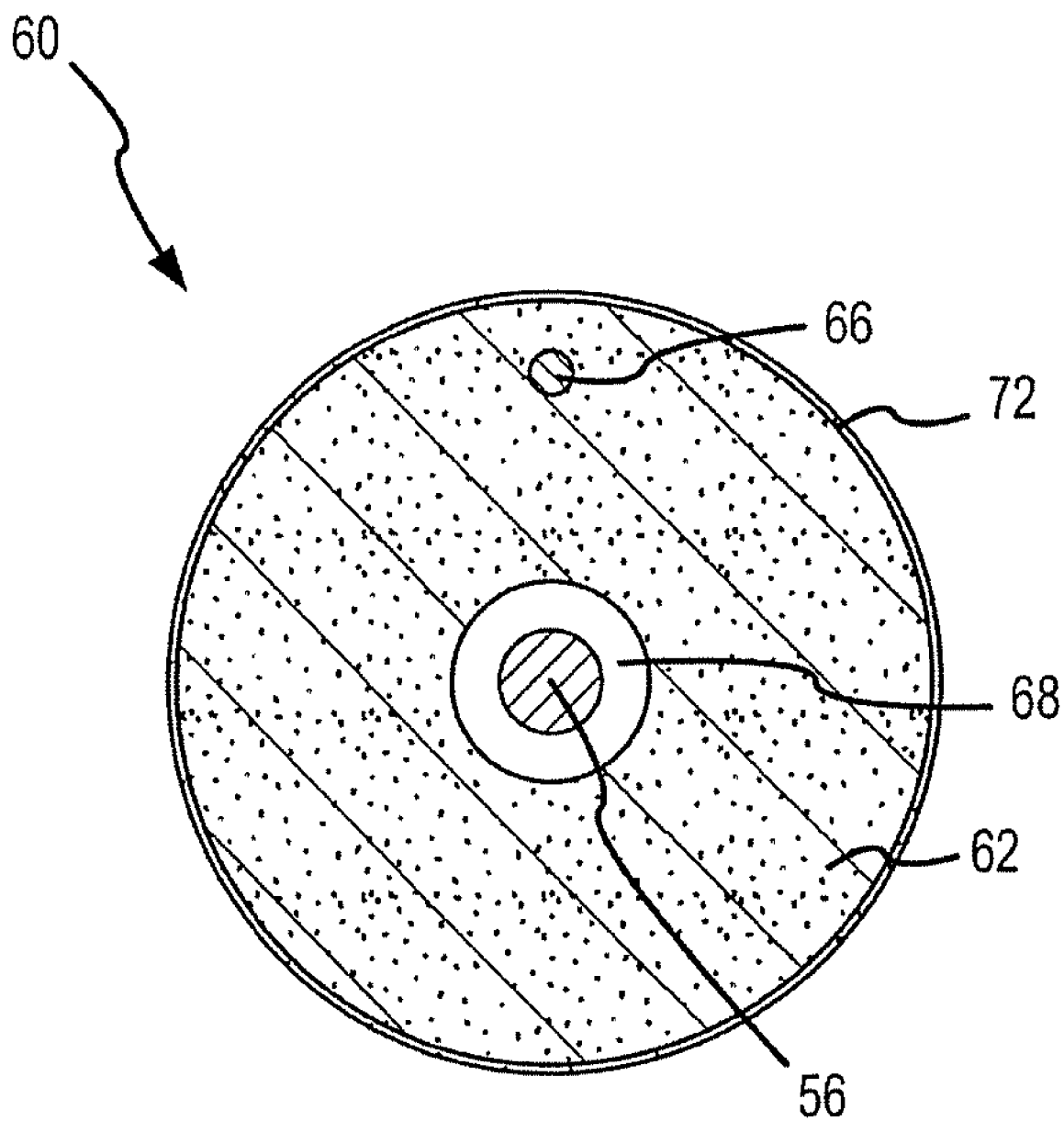
FIG. 20 is a cross-section taken along line 20-20 of FIG. 18, and further illustrating the use of an outer membrane which may help maintain the integrity of the stimulation lead when emplaced, as well as to control the rate at which the constituents incorporated within the dissolvable matrix are allowed to diffuse into the invertebral disc.

Referring now to FIGS. 18-20, yet another embodiment of the present invention is illustrated in the form of stimulation lead 60. For some treatments, it may be necessary to leave the stimulation lead emplaced within the invertebral disc for an extended period of time; however, for various reasons, it may not be possible to keep the stimulation lead emplaced for the amount of time to provide optimal treatment. In order to solve this particular problem, the embodiment of FIG. 18 contemplates the use of various chemical agents/medications and nutrients incorporated within a dissolvable matrix that forms the body 62 of the stimulation lead 60. The electrodes 64 as well as the conductor(s) 66 could be formed with the dissolvable matrix in a molding process whereby a particular shape and size stimulation lead could be produced. The electrodes 64 could function the same as the electrodes 22 discussed above and could be produced in any desired pattern and wiring arrangement. The dissolvable matrix can be made of a material that is biomedically acceptable for enabling a time release of the chemical agents/medications and nutrients mixed within the matrix. The matrix is preferably a solid yet flexible material, allowing the stimulation lead to be steered with the use of an insertable stylet 56 which could be provided through the central lumen 68. However, it shall be understood that this central lumen 68 is optional, and the matrix may be manufactured of a material which is durable yet flexible enough allowing the practitioner to steer the stimulation lead without the use of a stylet. Accordingly, FIG. 19 illustrates another embodiment wherein there is no lumen present, and a predetermined bend angle is formed in the stimulation lead enabling the lead to take the desired path through the disc when emplaced. Once inserted into the disc, the matrix would dissolve and the regenerating chemicals/medications and nutrients would slowly diffuse into the surrounding disc tissue leaving only the electrodes 64 and conducting wire(s) 66 to be removed at some later time.

With the embodiment shown in FIGS. 18 and 19, an infusion pump would not be required, and would thereby also allow for the subcutaneously placed pulse generator (IPG) to be significantly smaller. Similar to the combined pump/pulse generator device described above, this much smaller pulse generator could be rechargeable, or be powered by a battery source as desired.

In a modification to the embodiment of FIG. 18, it is also contemplated within the scope of the present invention that a stimulation lead can simply comprise a dissolvable matrix having a desired combination of chemical agents/medications and nutrients, and no electrodes incorporated within the lead. In some cases, stimulation by an electromagnetic field may be unnecessary to achieve the desired regenerative and/or pain relieving disc response.

FIG. 20 illustrates the designated cross-section of the device in FIG. 18. Additionally, FIG. 20 illustrates the use of an optional outer membrane 72 which could serve multiple purposes. One purpose for the membrane 72 would be to support the structural integrity of the matrix material of the body 62, thereby providing additional support for when the stimulation lead was emplaced. Additionally, this membrane 72 could serve as an osmotic membrane to help meter the rate at which the chemical agents/medications and nutrients were allowed to diffuse into the surrounding tissue. Thus, in addition to the matrix having a predetermined rate of diffusion, the membrane 72 could be used as an additional means to control the rate at which the chemical agents/medications and nutrients were delivered to the surrounding tissue. It is further contemplated that if the membrane 72 is provided only for structural support to the lead when emplaced, the membrane could be made of a material that quickly dissolves after being emplaced within the disc and the diffusion rate would be entirely controlled by the particular diffusion characteristics of the matrix.

Figure 21:
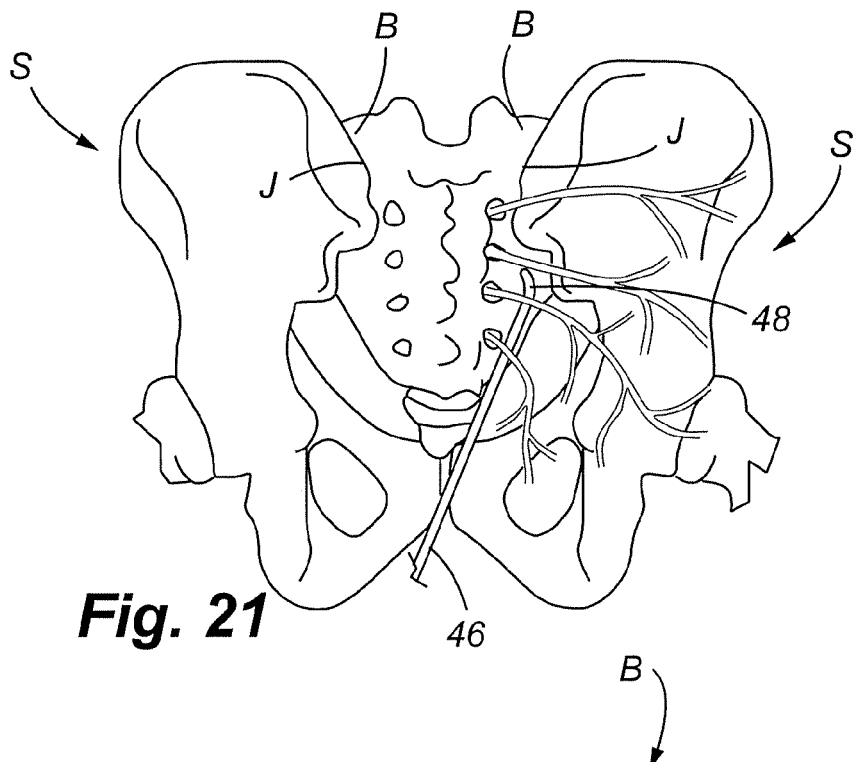
FIG. 21 is a posterior/dorsal view of the sacroiliac region with an introducer needle being positioned for insertion along the SI joint.
Figure 22:
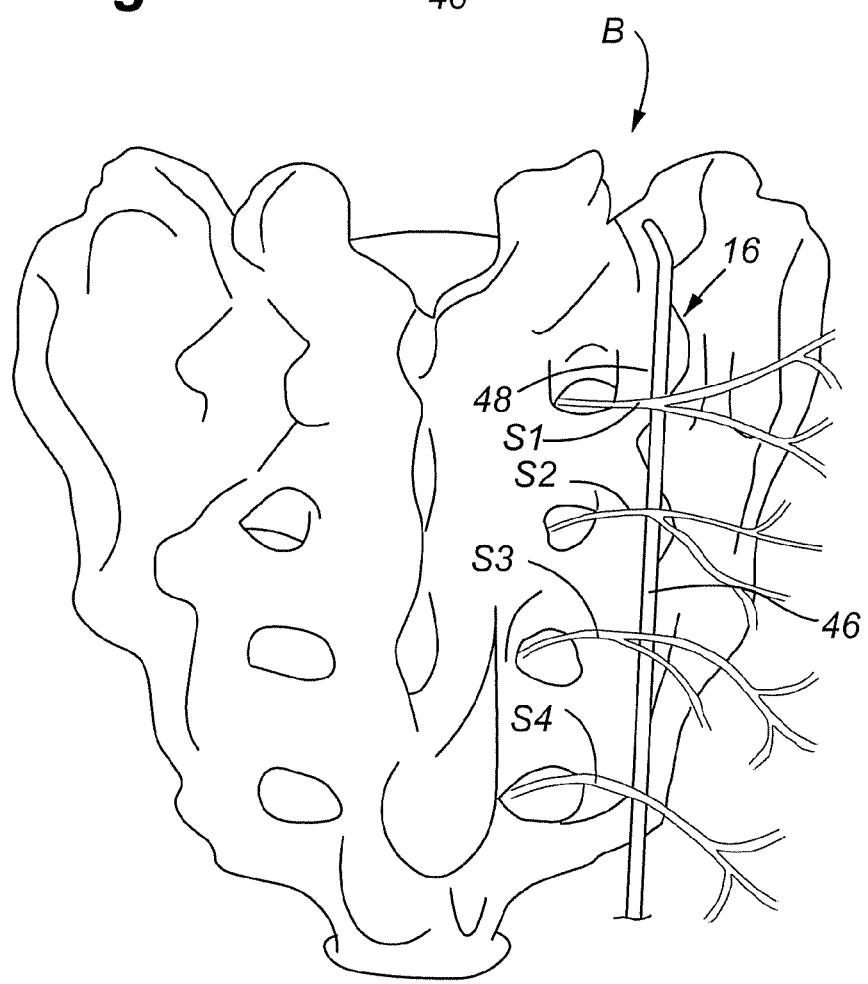
FIG. 22 is an enlarged posterior/dorsal view of the sacrum bone showing the introducer needle fully inserted.
Figure 23:
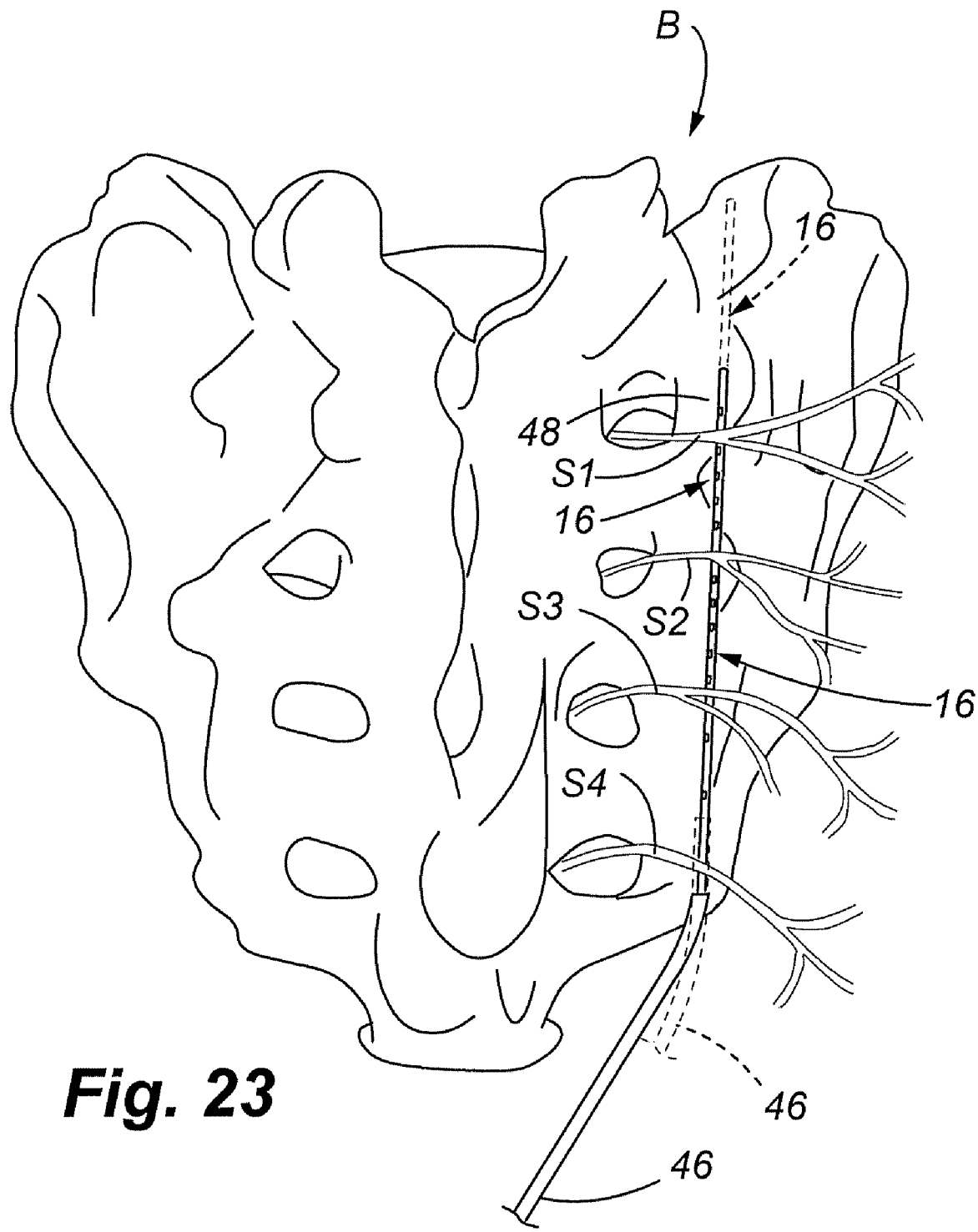
FIG. 23 is another enlarged anterior view of the sacrum bone showing the introducer needle withdrawn a selected length thereby exposing a specific number or group of electrical contacts/electrodes for denervation of selected sacral nerves.

Referring now to FIG. 21, in another aspect of the present invention, a stimulation device may be used to treat SI joint ailments. FIG. 21 specifically illustrates a posterior view of the sacroiliac region with an introducer needle positioned for insertion along the sacroiliac region to a targeted area adjacent the SI joint J. Referring also to FIG. 22, an enlarged posterior view of the sacrum bone B is shown wherein the introducer needle 46 has been fully inserted. In accordance with a method of the present invention for treatment of the SI joint, the introducer needle 46 is first inserted through the skin below and slightly medial to the inferior aspect to the SI joint and directed towards the inferior lateral edge of the sacrum (Brad show on Fig). The introducer needle 46 is advanced to contact the dorsal aspect of the sacrum at the posterolateral edge. As shown, the needle 46 may have a slight curvature near the distal end thereof, shown as curve or bend 48, and the curvature of the bend 48 is then utilized to advance the needle lateral to the sacral foramen and medial through the dorsal aspect of the SI joint. The needle 46 remains in contact with the periosteum along the entire curvature of the sacrum. The needle tip ultimately advances to the superior edge of the sacrum lateral to the sacral foramen and medial to the SI joint. Appropriate positioning of the introducing needle is confirmed preferably both on Antero-posterior (AP) as well as lateral views. The stimulation lead 16 is then inserted through the introducer needle 46 until reaching the distal tip 48 of the introducer needle. The stimulation lead 16 is held in place by maintaining pressure on the lead. Referring now to FIG. 23, the introducer needle 16 is withdrawn along a selected length of the stimulation lead 46 to expose the active number of electrodes 22 necessary to denervate the sacral nerve innervation to the SI joint. The dotted lines shown in FIG. 23 for lead 16 represent the initial position of the lead after the needle 46 is withdrawn. After the lead 16 is exposed, local anesthetic and/or neurolytic agents and/or proliferant agents such as, but not limited to, phenol or alcohol, or Dextrose respectively could be injected through one or more of the infusion ports. The electrodes 22 may then be activated to ablate the surrounding neural tissue. The dotted lines for needle 46 in FIG. 23 represent the position of the needle after it has been withdrawn and the lead is ready for activation. The solid lines in FIG. 23 represent the next position of the lead 16 and needle 46 wherein both have been further withdrawn for purposes of conducting another activation to further denervate tissue, such as a circumstance when the initial ablation did not effectively cover the desired area of tissue.

With respect to the specific construction of the stimulation lead for use in a method of treating the SI joint, it may be constructed in the same manner as disclosed with respect to the prior description for treatment of a disc. More specifically, a stimulation lead may be selected having the most desirable arrangement of electrodes for the most optimal denervation of the targeted neural tissues.

The sacral nerves illustrated in FIG. 23 include the lateral branches S1, S2, S3 and S4. In order to denervate each of the lateral branches, it may be required to sequentially apply energy to the stimulation lead as the introducer needle is repeatedly withdrawn along the path of insertion. Because of the variation of sacral anatomy, successful denervation may require two or more separate needle insertion angles in order to denervate the S1-S4 lateral branches. However, as discussed below with respect to the embodiments having multiple lead elements, it may be possible to avoid such multiple needle insertions. In addition to denervation of the sacral lateral branches, it may also be advantageous to denervate the L5 dorsal ramus as well as the L4 medial branch since there is some innervation to the SI joint from both of these additional nerve structures.

Although the figures show treatment along one side of the sacrum, it shall be understood that the same procedure may be repeated for treatment of the other side of the sacrum, by placement of the introducer needle in a symmetrical fashion on the corresponding opposite or contralateral side of the sacrum. In addition to electrical stimulation, it is also contemplated with respect to the method of treatment of the SI joint to also provide infusion in a combined electrical stimulation and chemical/drug infusion device. For example, infusion of collagen proliferants could be included in the method of treatment by use of a selected device including any one of the above-disclosed embodiments. Infusion of collagen proliferants such as dextrose, growth factors, and other nutrients may accelerate the healing process for some SI joint ailments. Depending upon the diagnosed ailment, infusion alone may be appropriate for the treatment, or in combination with some neural tissue ablation or stimulation. It is also contemplated in the method of the present invention to enhance neurolytic lesion size by infusion of substances such as Phenol, alcohol, and glycerin.

FIG. 24 illustrates yet another preferred embodiment of the present invention. In this embodiment, the stimulation lead has a substantially uniform curvature over a selected length of the stimulation lead. The amount of curvature provides a desired angle for extending the stimulation lead within the targeted area of the body. Additionally, the distal end 20 of the stimulation lead is similar to what is shown in FIGS. 4 and 6, and therefore may have an additional bend that assists the medical practitioner in steering the stimulation lead once it has exited the distal end of the introducer needle 32. This particular shaped stimulation lead may also be advantageous in conducting treatment of the SI joint as discussed above with respect to FIGS. 21-23.

FIG. 25 illustrates the stimulation device of FIG. 24 for purposes of treatment of vertebral structures other than a disc, such as ventral vertebral structures that are to be ablated.

FIG. 26 illustrates yet another preferred embodiment of the present invention wherein the stimulation lead is substantially liner or straight, and a stylet 76 is placed through a central lumen of the stimulation lead. For the embodiment of FIG. 26, the stylet 76 may be used to steer the stimulation lead, and to provide the necessary stiffness to the stimulation lead during emplacement. Once the stimulation lead has been manipulated to the desired position, the stylet 76 can be removed while keeping the stimulation lead stationary. Then, the desired electrical stimulation procedure can be conducted along with any desired infusion.

Figure 27:
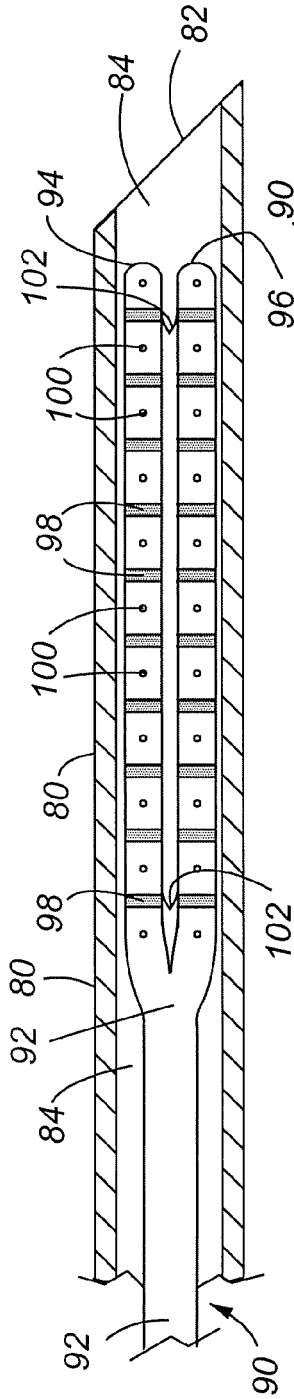
FIG. 27 is illustrates yet another preferred embodiment wherein the stimulation lead has a pair of deployable stimulation elements.
Figure 28:
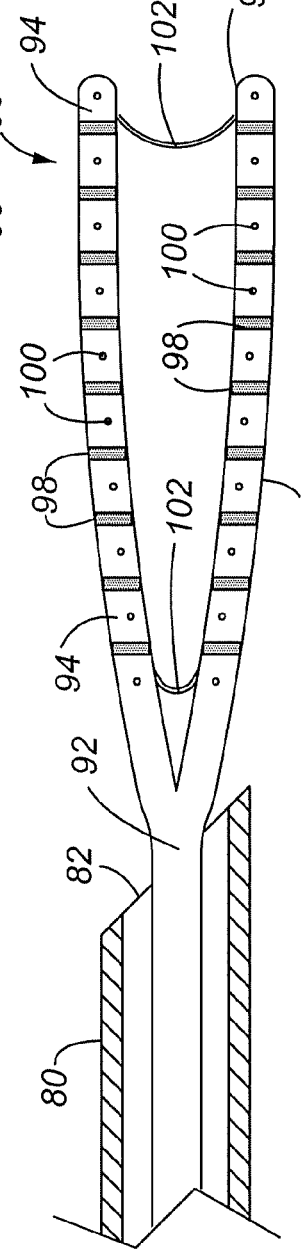
FIG. 28 illustrates the embodiment of FIG. 27 and showing the stimulation elements deployed.

FIGS. 27 and 28 illustrate yet another preferred embodiment of the present invention. In this embodiment, an introducer needle 80 having a sharp distal tip 82 may be used to introduce the stimulation lead into the body. Once the introducer needle has been located, the stimulation lead 90 is then passed beyond the distal tip 82 of the introducer needle and placed on or near the targeted tissue. Alternatively, the introducer needle may be withdrawn and pressure maintained on the stimulation lead to keep the lead in the desired position. The stimulation lead in this embodiment has a pair of stimulation elements 94 and 96 that are deployed once the stimulation lead exits the distal end of the introducer needle. The stimulation elements 94 and 96 share a common base 92. As with the other embodiments, the stimulation lead 90 may also include a desired arrangement of electrodes 98 and infusion ports 100. One or more spring or deploying elements 102 are positioned between and attached to the respective stimulation elements. As shown in FIG. 28, the deploying elements 102 can be in the form of curved springs, similar to leaf springs, which have enough spring force to spread or separate the stimulation elements of 94 and 96 away from one another, yet the springs can be collapsed to enable the stimulation lead to be placed back within the introducer needle or sheath. when the procedure is complete. Also, the spring elements 102 provide structural support to the stimulation elements in their deployed position to prevent excessive spread or displacement. Particularly in less dense tissue, it is advantageous for the stimulation elements to maintain their deployed configuration without further spread or displacement which might otherwise generate a burn lesion that is too large or a burn lesion that is not sufficiently concentrated. With respect to electrical stimulation, excessive spread or displacement of the leads may result in a weakened electrical field that does not adequately stimulate the targeted tissue. As shown, the stimulation elements are spread in a manner such that they extend radially beyond the diameter of the introducer needle. The extent to which the stimulation elements are spread or separated from one another can be dictated based on the desired spacing of the stimulation elements for the particular procedure being conducted. It should also be understood that only one spring element or more than two spring elements can be used between each pair of stimulation elements to optimize the desired configuration of the stimulation elements. Additionally, the particular type of material and the size of the springs 102 may be selected to match the intended purpose of the stimulation lead where it may be desired to deploy the stimulation elements in various configurations. The embodiment of FIG. 28 is well suited for neural ablation wherein it may be desirable to ablate a relatively large area, thereby minimizing or eliminating the need to reintroduce the introducer needle along with multiple stimulation lead deployments.

With respect to the specific construction and material used for spring elements 102, it is contemplated that the spring elements can be made from either metallic or thermoplastic materials. The particular material chosen should have elastomeric/resilient characteristics which allows the spring elements to expand or open when the stimulation elements are freed from the insertion needle, but also allows the spring elements to collapse without undue force when the stimulation lead is withdrawn and placed back within the introducer needle. As shown in FIG. 28, the particular spread of the stimulation elements allows the stimulation lead to cover a larger area than would be possible if just a single stimulation element were present.

Figure 29:
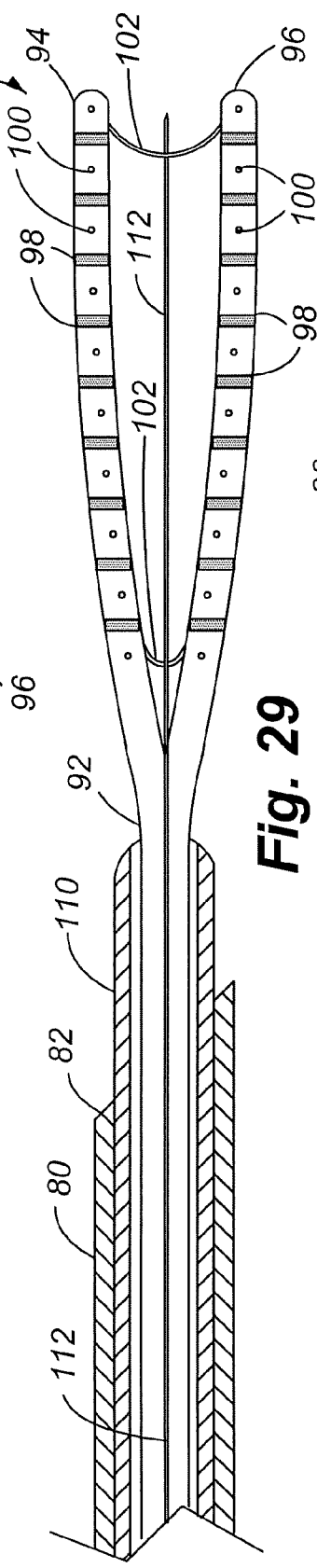
FIG. 29 illustrates the embodiment shown in FIGS. 27 and 28 but further including a central stylet to assist the guidance of the stimulation lead.

FIG. 29 illustrates the embodiment of FIG. 28, but further adds a stylet 112 which can be used to guide the placement of the pair of stimulation elements. FIG. 29 also illustrates a sheath 110 that is placed within the introducer needle 80, and the stimulation lead is housed within the sheath. In accordance with a procedure for use of the embodiment of FIG. 29, the introducer needle 80 is located first, and then the sheath 110 is extended beyond the distal end 82 of the introducer needle. The sheath is located, and then the stimulation lead 90 is extended beyond the distal end of the sheath 110. The sheath may be a very flexible material, and the use of the stylet 112 captured within the sheath adjacent the stimulation lead allows the stylet 112 to then precisely position the stimulation lead. Alternatively, it is also contemplated that a procedure could be conducted wherein the sheath is moved to the most distal position within the body, and then the stimulation lead 90 is held in place while the sheath 110 is then withdrawn back over the stimulation lead 90, thereby exposing the stimulation elements 94 and 96 and allowing them to deploy. Yet further in the alternative, a procedure can be conducted whereby the introducer needle is moved to the most distal position within the body, the needle is withdrawn while the sheath and stimulation lead are held in place, and then the sheath is withdrawn while the stimulation lead is held in place. As with the embodiment of FIG. 28, once the ablation or electrical stimulation is completed, the stimulation lead 90 is then withdrawn back into the sheath 110, the sheath 110 is withdrawn back into the needle 80, and then the needle is withdrawn from the body.

Figure 30:
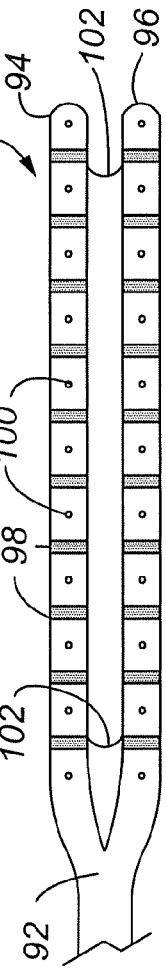
FIG. 30 illustrates yet another preferred embodiment of the present invention wherein the pair of stimulation elements are more closely spaced, and are substantially parallel to one another.

FIG. 30 illustrates yet another preferred embodiment of the present invention wherein the pair of stimulation elements 94 and 96 are more closely spaced to one another and maintain a very parallel relationship with one another. The stimulation lead shown in FIG. 30 is especially adapted for conducting electro stimulation along the spinal cord.

Figure 31:
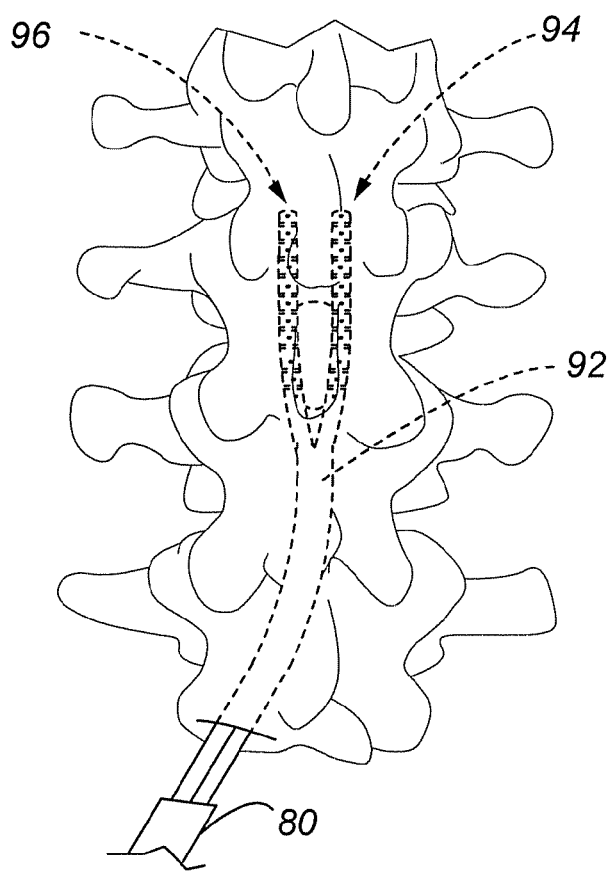
FIG. 31 is a fragmentary perspective view of a portion of a spine and the stimulation lead of FIG. 30 for purposes of conducting a procedure for stimulation of the spinal cord.
Figure 32:
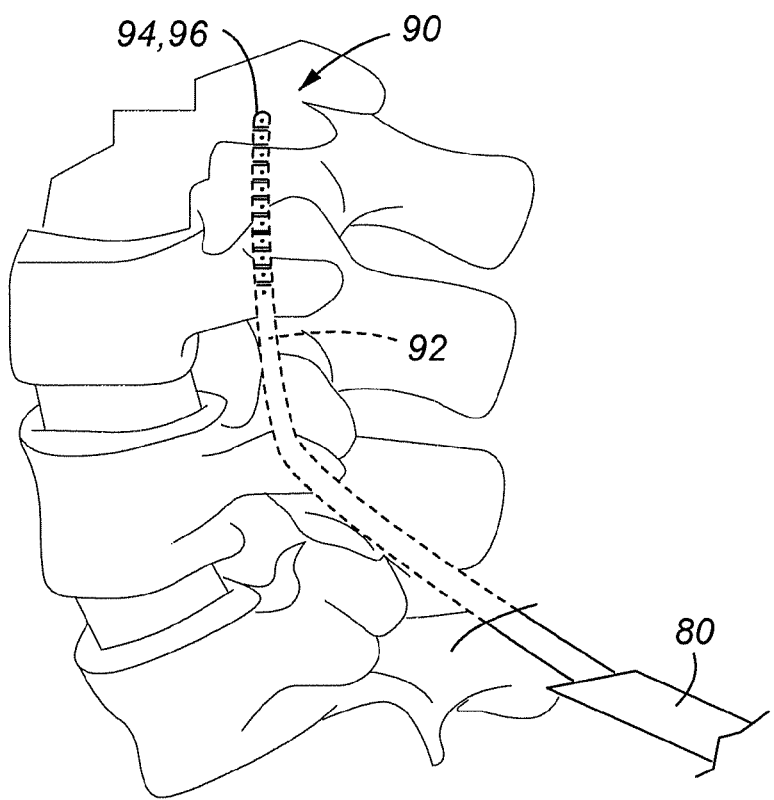
FIG. 32 is a lateral or side view of the stimulation lead of FIG. 31 for the procedure shown in FIG. 31.

FIGS. 31 and 32 illustrate the stimulation lead of FIG. 30 used in the procedure for electrical stimulation of the spinal cord and/or selected neural tissue adjacent the spinal cord. Although FIGS. 31 and 32 illustrate the stimulation lead for placement within the epidural space between vertebral structures, it shall be understood that the stimulation lead is well suited for treatment of other areas along the spine to include the ventral canal along the posterior longitudinal ligament, ventral dura, and the posterior aspect of the disc.

FIG. 33 illustrates yet another embodiment of the present invention wherein the stimulation lead 90 includes 3 stimulation elements, 120, 122, and 124. The embodiment of FIG. 33 also illustrates a plurality of spring elements 102 placed between the stimulation elements. FIG. 34 is an end view illustrating the linear spaced relationship between the stimulation elements 120, 122 and 124. For this particular embodiment, the provision of three stimulation elements may provide yet a larger area of tissue that may be ablated or otherwise treated, noting that the spread of the stimulation elements can cover yet a larger area depending upon the spread or gap between the stimulation elements.

FIG. 35 illustrates yet another embodiment similar to the embodiment of FIG. 33, wherein three stimulation elements are present, but a different pattern of electrodes 98 and infusion ports 100 are provided. Additionally, the embodiment of FIG. 35 does not require the incorporation of spring elements 102. Rather, the elastomeric/resilient nature of the stimulation lead material itself is enough for the stimulation elements to spread once they are freed from the distal end of the insertion needle. Highlighted area 126 on the base 92 of the stimulation device may be particularly elastomeric/resilient such that the stimulation elements 120, 122, and 124 spread in the depicted liner or flat orientation. Thus, the nature of the stimulation lead material can dictate the ultimate deployed orientation of the stimulation elements without the use of spring elements.

FIGS. 36 and 37 illustrate the embodiment of FIG. 35 stored within the introducer needle. The stimulation elements 120, 122, and 124 are bundled together in order that the three stimulation elements may conveniently fit within the introducer needle. However, when the stimulation lead is deployed as shown in FIG. 35, the elastomeric/resilient nature of the material at highlighted area 126 causes the stimulation elements to spread.

FIG. 38 illustrates yet another embodiment of the present invention wherein three stimulation elements 120, 122, and 124 are provided, yet in their deployed position, the stimulation elements maintain a triangular configuration. Thus, this embodiment represents yet another arrangement of the stimulation elements that optimizes heat transfer or electrical stimulation of targeted tissue to be treated.

In order to stiffen or otherwise control any of the stimulation leads 90 shown in the embodiments of FIGS. 33, 35, and 38, a stylet (not shown) may also be used in the same manner as the stylet 112 shown and described with reference to FIG. 29. Accordingly, a stylet captured within the needle or sheath adjacent the stimulation lead 90 allows the stylet to assist in precise placement of the stimulation lead.

FIGS. 40-42 illustrate yet another preferred embodiment of the present invention wherein the stimulation device 90 includes a pair of stimulation elements 94 and 96 that are deployed by a different mechanism. The stimulation elements are deployed by use of a distal keeper or tab 130 that secures the distal ends of the stimulation elements. A tether or line 132 is attached to the tab 130. Once the stimulation elements are located, the tether 132 is withdrawn while applying force to the stimulation lead to prevent it from withdrawing with the tether. Accordingly, the stimulation elements spread apart from one another in the configuration shown. Optionally, the tab 130 may have a pointed distal tip that allows the stimulation lead to be better guided during emplacement. FIG. 43 also illustrates the deployed position of the stimulation lead for the embodiment of FIGS. 40-42.

FIG. 44 illustrates yet another preferred embodiment of the present invention. In this embodiment, a stimulation lead 142 is shown protruding from a sheath 140. The sheath is initially housed within an introducer needle 80. In the position shown in FIG. 44, the introducer needle has been withdrawn or the sheath has been advanced beyond the needle thus exposing the stimulation lead 142. The stimulation lead 142 is not deployed from within the sheath and rather, the stimulation lead remains exposed. The stimulation lead in the embodiment of FIG. 44 has two separate stimulation elements, namely, elements 144 and 146. These elements have respective proximal ends 145 and 147 that are secured to a distal cap 141 of the sheath. The stimulation elements 144 and 146 are preferably conductive along their entire length and therefore, form respective continuous electrodes. The stimulation elements 144 and 146 may be powered by control wires 150 and 152 that extend within the sheath 140 and proximally back to a stimulation source 14. Alternatively, the control wires can be eliminated and the sheath itself can be used as the conductor to provide power to the stimulation elements 144 and 146 since the proximal ends 145 and 147 in contact with the cap 141 can form continuous electrical pathways. However, if the sheath is used as the conductor, the outer surface is insulated to prevent the sheath from also being an active electrical element to prevent it from heating or electrically stimulating the surrounding tissue. If control wires 150 and 152 are used to provide power to the stimulation elements, then each may be separately controlled to provide the requisite electrical current to each element. A central stylet or needle 148 extends through a slot in the end cap 141 of the sheath and between the stimulation elements 144 and 146. The distal ends of the stimulation elements are attached to the distal tip of the stylet 148. Additionally, the stylet 148 may be an active stimulation element by being electrically powered by either by a control wire or by the sheath in contact with the stylet. Referring now to FIGS. 45 and 46, in order to deploy the stimulation elements in a desired configuration, the sheath 140 is moved in the distal direction as shown by directional arrow A while the stylet 148 is held stationary. As shown in FIG. 45, as the sheath is advanced, the stimulation elements are separated from one another. FIG. 46 shows the sheath further advanced such that the stimulation elements are fully deployed. Once the stimulation elements are in the desired configuration, the procedure can be conducted to heat or electrically stimulate the surrounding tissue. After the procedure, sheath 140 is withdrawn allowing the stimulation elements to collapse back on the stylet 148. The sheath may then be withdrawn back into the introducer needle. The embodiment of FIG. 144 is especially adapted for use in a neuro-ablation procedure where it is desired to ablate a relatively large area. The heated tissue surrounding the stimulation elements and stylet will coalesce thus creating one burn lesion. Since the stimulation elements may be deployed at variable positions depending upon how far the sheath is advanced over the stylet, the particular lesion size, or size of the electrical field for electrical stimulation, can be selected by selective advancement of the sheath.

Figure 47:
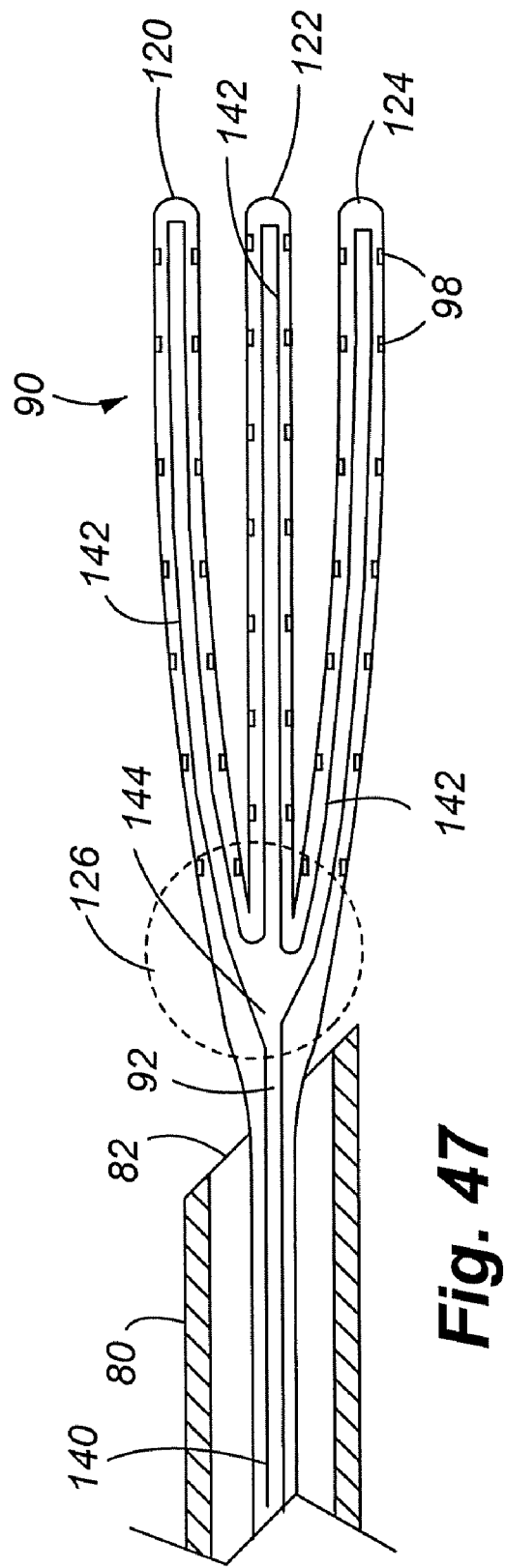
FIG. 47 is a cross sectional view of yet another embodiment of the present invention wherein hydraulic pressure is used to deploy the stimulation elements by fluid which is pumped into a central lumen of the stimulation lead.

FIG. 47 illustrates in cross section yet another embodiment of the present invention. In FIG. 47, the stimulation lead is similar to the prior embodiments illustrated in FIGS. 30, 33 and 35, with the exception that a different mechanism is used to deploy the stimulation elements in the desired configuration. In FIG. 47, a central lumen or opening 140 extends through the base 92 of the stimulation lead. The central lumen then separates into respective branches 142 that extend along a selected length of each of the stimulation elements 120, 122 and 124. The central lumen 140 may be enlarged in the area 126 thus forming a larger central chamber or opening 144. After the introducer needle 80 has been withdrawn to expose the stimulation elements, a fluid source is pumped into the central lumen 140 thereby pressurizing the central lumen 140 and each of its branches 142 with the pressurized fluid. The stimulation lead in this embodiment is made of a material that some degree of flexibility, and may have some degree of elasticity such that pressurizing the central lumen and branches 142 causes some change in shape of the stimulation lead especially around the area 126. Of course in this embodiment, the respective branches 142 terminate within each of the stimulation elements to prevent the pressurized fluid from escaping. Therefore, the hydraulic force of the fluid that fills the central lumen 140 and its branches 142 expands the stimulation elements in the desired configuration. The particular shape of the reservoir 144, as well as the size and shape of the branches 142 will dictate the deployed configuration of the stimulation elements. Selective application of varying hydraulic pressures can be used to modify the shape of the stimulation lead and therefore to optimize the procedure to be conducted.

Figure 48:
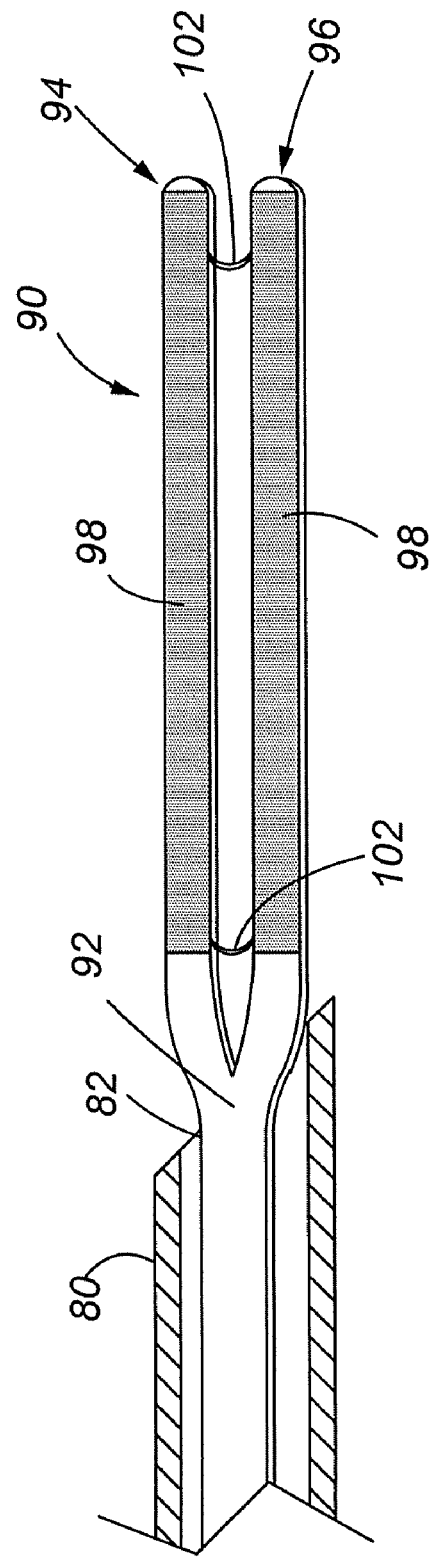
FIG. 48 illustrates yet another embodiment of the present invention wherein the stimulation lead is substantially flat or planer, and the stimulation elements include continuous electrodes that extend along the length of the elements.

FIG. 48 illustrates yet another embodiment of the present invention. In this embodiment, the stimulation lead 90 comprises a pair of stimulation elements 94 and 96, similar to those illustrated in FIGS. 28 and 29; however, the stimulation elements in this embodiment instead of having a tubular configuration are substantially planer or flat. Also in this embodiment, similar to the embodiment of FIG. 44, the stimulation elements are continuous electrodes along the length of the stimulation elements as opposed to separately spaced electrodes. In some procedures, it may be preferable to have flat stimulation elements which can be placed in very narrow passages or openings formed in the tissue from the introducer needle or sheath, yet it is still desirable to have a plurality of stimulation elements that may be deployed in a desired configuration to increase the size of the lesion created by ablation, or the size of the electrical field to be applied to the targeted tissue. In order to stiffen the stimulation lead 90, a stylet (not shown) may also be used in the same manner as the stylet 112 shown and described with reference to FIG. 29.

FIGS. 49 and 50 illustrate yet another preferred embodiment of the present invention wherein the stimulation lead 160 is made of a very flexible and elastomeric material, such as a synthetic rubber. The introducer needle 80 is preferably first advanced to the desired location where the procedure is to be conducted, and then the needle 80 is withdrawn thus exposing the stimulation lead 160 as shown in FIG. 49. The stimulation lead 160 has a flexible and elastomeric body 162, and a plurality of electrodes 164 are secured to the outer surface of the body 162. The electrodes 164 may be electrical wires that have a zigzag appearance prior to the stimulation lead being inflated as shown in FIG. 49. The electrodes 164 are not secured along their entire lengths to the body 162, but rather, at discrete points and there is some amount of slack in the electrodes between the points of connection which allows the electrodes to displace without breakage when the stimulation lead is inflated. In FIG. 150, the stimulation lead is illustrated wherein a pressurized fluid source inflates the stimulation lead, and the amount of supplied fluid dictates the shape of the stimulation lead in its deployed position. As the stimulation lead is inflated, the body 162 increases in size and the electrodes 164 displace to a desired pattern. In the example of FIG. 50, the electrodes 164 extend circumferentially around the body 162 in a plurality of bands that are spaced from one another. The interior of the stimulation lead may be hollow like a balloon, or the interior of the stimulation lead may have a lumen such that the stimulation lead has a much greater thickness. Additionally, the inflatable stimulation lead of this embodiment may have one or more stimulation elements provided in a configuration like the embodiment illustrated in FIGS. 38 and 47.

Based upon the foregoing, the present invention provides a combination electrical and chemical stimulation lead especially adapted for treatment of many types of ailments to include, disc ailments SI joint ailments, and other spine ailments to include treatment of structures that have large and diffuse innervations such as, but not limited to, the superior hypogastric plexus, sympathetic chain, ganglion impar, and others.

The various embodiments provide a treating physician with stimulation leads of various configurations, which optimizes a physician's ability to precisely position the stimulation lead, as well as to precisely direct both electrical and chemical stimulation.

While the above description and drawings disclose and illustrate embodiments of the present invention, it should be understood that the invention is not limited to these embodiments. Those skilled in the art may make other modifications and changes employing the principles of the present invention, particularly considering the foregoing teachings. Therefore, by the appended claims, the applicant intends to cover such modifications and other embodiments.

What is claimed is:

1. A method of managing SI joint pain in a sacrum of a patient, said method comprising the steps of:
   providing a stimulation lead having at least one electrode selectively placed along said stimulation lead;
   providing an introducer needle having a curvature along its length and a bent distal end;
   inserting the introducer needle along a path of insertion into a patient defined by aligning the introducer needle in a position medial to an inferior aspect of the SI joint and directed towards an inferior lateral edge of the sacrum;
   advancing the introducer needle along a curve of the sacrum in close proximity to a periosteum, lateral to a sacral foramen and medial to the SI joint until reaching a superior aspect of the sacrum;
   inserting the stimulation lead in the introducer needle;
   placing pressure on the stimulation lead to maintain the lead in a first position;
   withdrawing the introducer needle along the path of insertion and along a selected length of the stimulation lead to expose said at least one electrode to denervate targeted tissue;
   activating said at least one electrode in order to denervate tissue surrounding the stimulation lead;
   withdrawing the stimulation lead to a second position and aligned along the path of insertion within the introducer needle;
   placing pressure on the stimulation lead to maintain the lead in the second position;
   withdrawing the introducer needle aligned along the path of insertion thereby exposing said at least one electrode on the stimulation lead; and
   further activating said at least one electrode in order to denervate tissue surrounding the stimulation lead.

2. A method, as claimed in claim 1, further including the step of:
   infusing through said stimulation lead at least one chemical selected from the group consisting of an anesthetic, a neurolytic, a proliferant, and a nutrient.

3. A method, as claimed in claim 1, wherein:
   said at least one electrode includes a plurality of electrodes spaced along a length of said stimulation lead.

* * * * *